US010007981B2

(12) United States Patent
Gangitano et al.

(10) Patent No.: US 10,007,981 B2
(45) Date of Patent: Jun. 26, 2018

(54) AUTOMATED RADIAL IMAGING AND ANALYSIS SYSTEM

(71) Applicants: Keith Joseph Gangitano, Morgan Hill, CA (US); David Preston Graton, Morgan Hill, CA (US)

(72) Inventors: Keith Joseph Gangitano, Morgan Hill, CA (US); David Preston Graton, Morgan Hill, CA (US)

(73) Assignee: Mountain Forge, Morgan Hill, CA (US)

( * ) Notice: Subject to any disclaimer, the term of this patent is extended or adjusted under 35 U.S.C. 154(b) by 241 days.

(21) Appl. No.: 15/206,265

(22) Filed: Jul. 9, 2016

(65) Prior Publication Data

US 2018/0012350 A1    Jan. 11, 2018

(51) Int. Cl.
*G06T 7/00* (2017.01)
*G01N 21/88* (2006.01)
(Continued)

(52) U.S. Cl.
CPC ......... *G06T 7/001* (2013.01); *G01N 21/8806* (2013.01); *G06Q 10/20* (2013.01); *G07C 5/0808* (2013.01); *G07C 5/0866* (2013.01); *H04N 5/2256* (2013.01); *H04N 5/247* (2013.01); *H04N 5/2628* (2013.01); *H04N 5/772* (2013.01); *H04N 7/181* (2013.01); *G06T 2207/30248* (2013.01); *G06T 2207/30252* (2013.01)

(58) Field of Classification Search
CPC ..... G06T 7/001; G06T 7/0008; G06T 7/0004; G06T 2207/30252; G06T 2207/30248; G06T 2207/30156; G06Q 10/20; G01N 21/8806; G01N 21/8851; G01N 2201/102; G07C 5/0866
See application file for complete search history.

(56) References Cited

U.S. PATENT DOCUMENTS 5,726,705 A * 3/1998 Imanishi ............ G01N 21/8806
348/92
6,266,138 B1 * 7/2001 Keshavmurthy .... G01B 11/303
356/237.2
(Continued)

FOREIGN PATENT DOCUMENTS

DE    102016013869 A1 *    5/2017
JP    09318337 A *    12/1997
(Continued)

*Primary Examiner* — John M Villecco

(57) ABSTRACT

A system for imaging and analyzing a vehicle may include a frame having a central passage, wherein the central passage is configured and dimensioned to allow a vehicle to pass through. The frame may include, for example, a pair of substantially vertical legs connected at the top by a cross member, wherein the legs and cross member define the central passage. One or more bollards may be positioned in front of and/or behind the frame. A plurality of cameras within the each leg, cross member, and/or bollard may be directed toward the passage to record video images of a passing vehicle. Integrated LED array panels may provide bands of light to aid in detection of surface anomalies, for example by simultaneous analysis of symmetrical sides of the vehicle.

17 Claims, 16 Drawing Sheets

(51) Int. Cl.
*G06Q 10/00* (2012.01)
*G07C 5/08* (2006.01)
*H04N 5/262* (2006.01)
*H04N 7/18* (2006.01)
*H04N 5/77* (2006.01)
*H04N 5/225* (2006.01)
*H04N 5/247* (2006.01)

(56) References Cited

U.S. PATENT DOCUMENTS

| | | | | |
|---|---|---|---|---|
| 6,320,654 B1 * | 11/2001 | Alders | ............... | G01N 21/8806 356/237.2 |
| 7,889,931 B2 * | 2/2011 | Webb | ................ | G01N 21/8806 382/141 |
| 8,712,893 B1 * | 4/2014 | Brandmaier | ........ | G06F 17/3028 705/35 |
| 8,767,075 B2 * | 7/2014 | Bianco | .................. | G07B 15/02 348/149 |
| 8,982,207 B2 * | 3/2015 | Jang | ..................... | B64F 5/0045 348/125 |
| 9,424,606 B2 * | 8/2016 | Wilson, II | .............. | G06Q 10/10 |
| 9,541,505 B2 * | 1/2017 | Kesler | ................ | G01N 21/8806 |
| 9,684,934 B1 * | 6/2017 | Wilson, II | .............. | G06Q 40/08 |
| 9,799,077 B1 * | 10/2017 | Wilson, II | .............. | G06Q 40/08 |
| 9,886,771 B1 * | 2/2018 | Chen | ...................... | G06T 7/0032 |
| 2007/0250232 A1 * | 10/2007 | Dourney, Jr. | .......... | G06Q 99/00 701/33.4 |
| 2012/0109660 A1 * | 5/2012 | Xu | ......................... | G06Q 10/06 705/1.1 |
| 2014/0201022 A1 * | 7/2014 | Balzer | ................ | G01N 21/8806 705/26.4 |
| 2016/0343251 A1 * | 11/2016 | Lee | ........................ | G08G 1/04 |
| 2017/0147990 A1 * | 5/2017 | Franke | .................. | G06Q 10/20 |
| 2017/0147991 A1 * | 5/2017 | Franke | .................. | G06Q 10/20 |
| 2017/0148101 A1 * | 5/2017 | Franke | .................. | G06Q 10/20 |
| 2017/0148102 A1 * | 5/2017 | Franke | .................. | G06Q 10/20 |

FOREIGN PATENT DOCUMENTS

| | | | |
|---|---|---|---|
| JP | 10009841 A | * | 1/1998 |
| JP | 2010185820 A | * | 8/2010 |
| JP | 2014066657 A | * | 4/2014 |
| JP | 2014081356 A | * | 5/2014 |

* cited by examiner

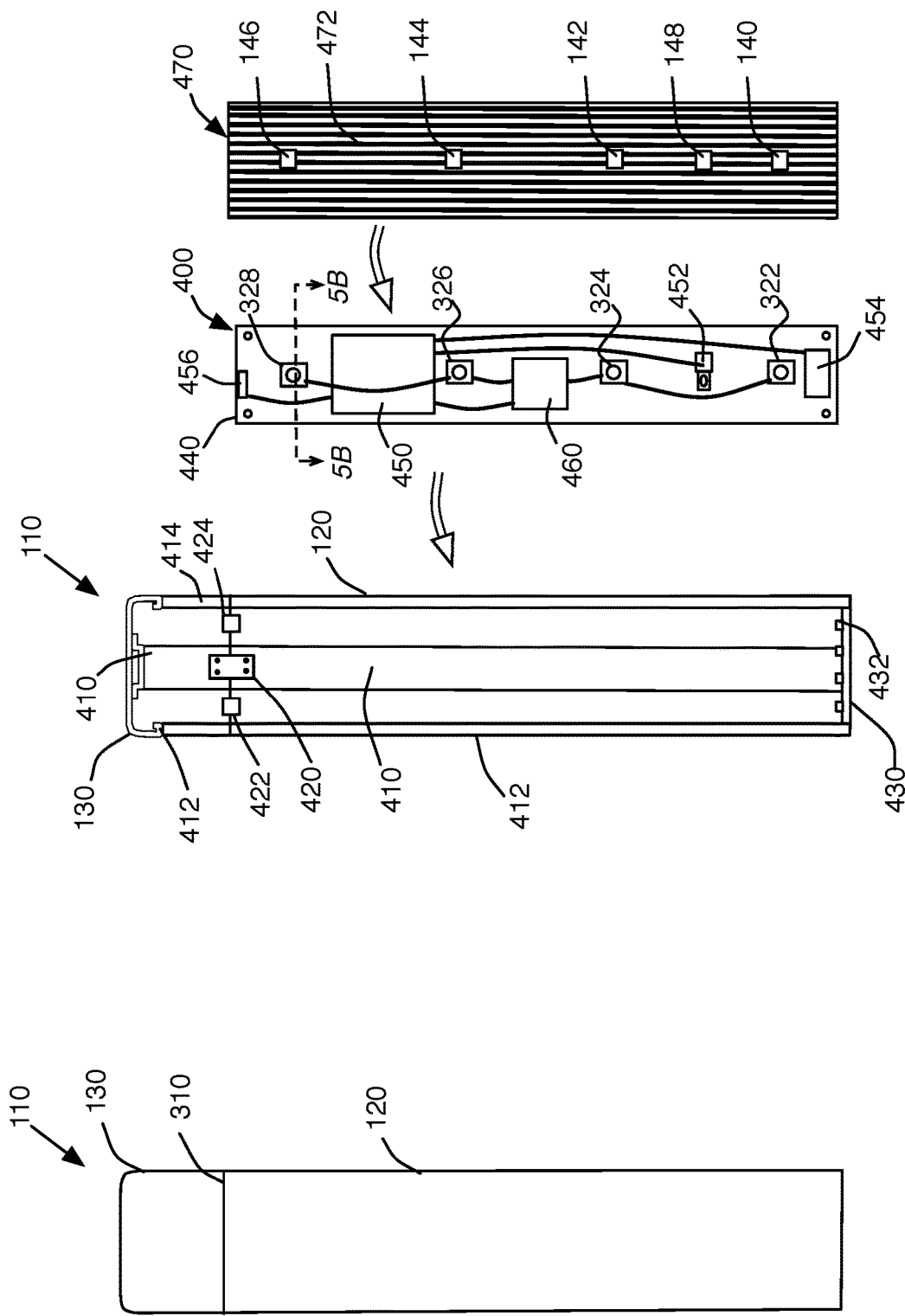

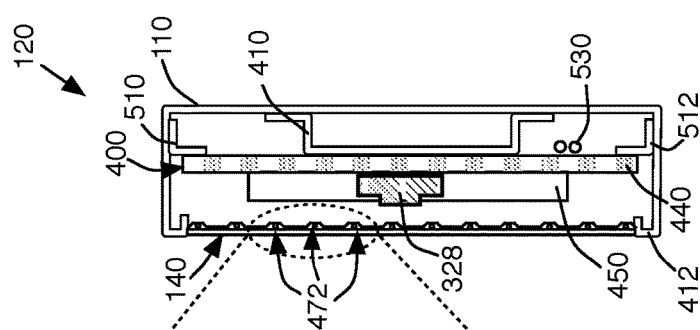
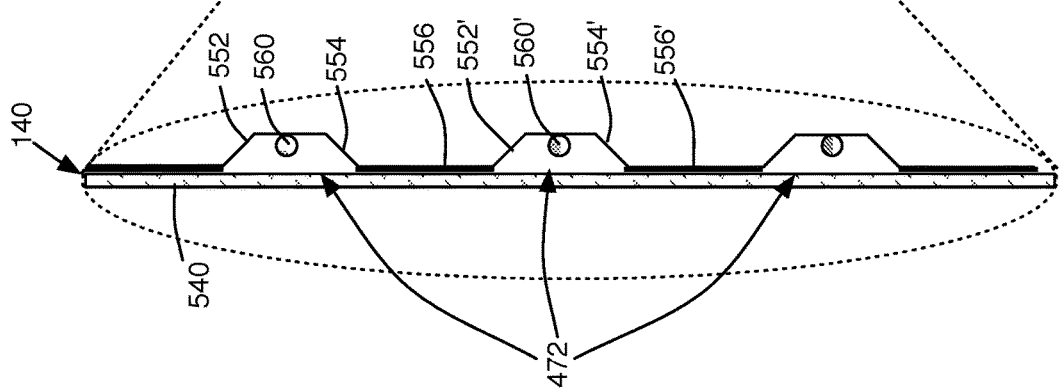
FIG. 5A
FIG. 5B

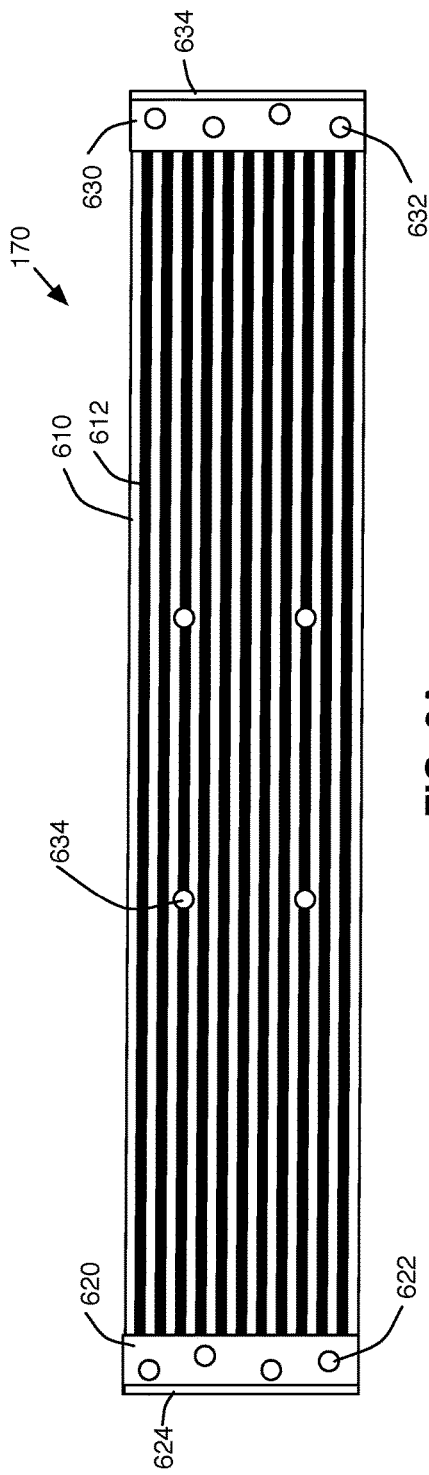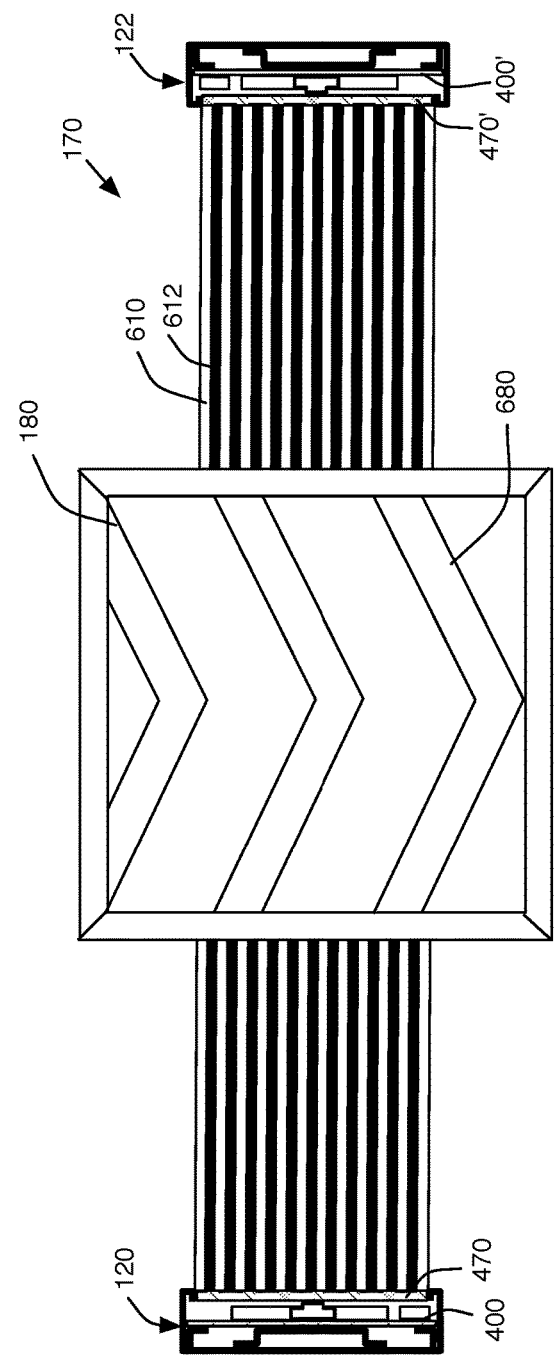

AUTOMATED RADIAL IMAGING AND ANALYSIS SYSTEM

TECHNICAL FIELD

The disclosed embodiments relate generally to imaging systems and methods, and in particular to systems and methods for detecting damage to a vehicle.

BACKGROUND

Unless otherwise indicated herein, the elements described in this section are not prior art to the claims and are not admitted to be prior art by inclusion in this section.

Currently the standard for discovering damage in a vehicle relies on human visual analysis, which is inherently flawed. The present invention controls for light and uses know characteristics of reflection to enable the detection of dents or deformities as small as 4-5 mm, for example. By using high definition cameras the system may provide an effective zoom function to differentiate between a smear of dirt, for example, and an actual scratch. The system may also be able to clearly identify damage to automobile wheels, windshields, and other areas.

Other existing solutions include an application for tablet devices that requires an employee to walk around the vehicle to record video. Such methods are not ideal, as small and even medium sized damage is difficult to photograph even when one knows what to photograph or record, much less when the user is attempting to discover unknown damage. Another suggested solution involves an array of digital cameras to be installed in the doorway of an existing building. This solution does not control for light nor does it account for variables like multiple cars where one may be blocking the other, or people or other obstructions.

Thus, there remains a need for a cost effective, flexible and powerful system and method for detecting damage on a vehicle.

SUMMARY

Automated radial imaging and analysis systems and methods described herein may use a combination of video and still photography to record and/or categorize the presence damage, or lack thereof, to a vehicle. In some embodiments, a vehicle imaging and analysis system may provide a detailed photo record of scratches, dings, dents, damaged wheels, and the like at the time when the care, custody and control of a vehicle passes from one entity to another. In some embodiments, a radial imaging and analysis system may work together with an on board diagnostics wireless transceiver, which may communicate the VIN of the vehicle and/or other identifying information, as well as volume of fuel, mileage, engine codes, GPS information, etc., and in some embodiments may trigger the dome lights on and off, e.g., in a rental car setting. Such parameters may be accessed, for example, by plugging a transceiver into an OBD II port on the vehicle and wirelessly transmitting data from the transceiver to the system.

In some embodiments, a system for imaging and analyzing a vehicle may include a frame having a central passage, wherein the central passage is configured and dimensioned to allow a vehicle to pass through. The frame may include, for example, a pair of substantially vertical legs connected at the top by an arched or horizontal cross member, wherein the legs and cross member define the central passage. One or more bollards, or posts, may be positioned in front of and/or behind the frame, e.g., at a distance of approximately two feet (or other desired distance) from the front and/or rear of each leg of the frame. A plurality of cameras within the frame, e.g., within each leg and the cross member, may be directed toward the passage to record video images of a vehicle passing there through. In some embodiments, one or more of the bollards may also include a camera, e.g., positioned to provide images of the front and/or rear of a vehicle as it passes through the system. In some embodiments, cameras in the front and/or rear bollards may also provide vehicle identification information, e.g., from an image of the vehicle license plate, bar code, auction number, or other indicia on the vehicle. In some embodiments, each of the plurality of cameras may be a video camera, e.g., a high definition or HDR camera for capturing high definition and/or high dynamic range video.

In some embodiments, the frame may also incorporate a light source, e.g., one or more LED panels or other light source or sources, for illuminating the passage to optimize video recording. In some embodiments, LED light panels are configured and dimensioned to emit elongated and substantially parallel bands of light, e.g., to aid in detection of dents, dings, or other anomalies in a vehicle body from captured video and/or still images of the vehicle when it moves thorough the central passage of the frame. Each LED panel may include, for example, a plurality of parallel elongated reflective channels, each of which housing an LED strip configured to illuminate the reflective channel and emit an elongated band or stripe of light. In some embodiments, each of the plurality of parallel channels may be separated by a black or opaque stripe or border, e.g., to provide contrast between adjacent light strips, thereby providing an array of parallel light bands or stripes. In some embodiments, a translucent cover, e.g., glass, Lucite, acrylic, polycarbonate or other transparent or semi-transparent material may be used to cover the LED strips.

In some embodiments, one or more sensors may also be disposed within the frame and/or bollards. For example, a motion detector in the cross member (or within one or more bollards or frame legs) may be used to detect the presence of a vehicle and activate the system. One or more of the bollards may also include, for example, a motion detector or trip sensor, e.g., to activate and/or deactivate the system and/or to begin or end recording of data as a vehicle enters and leaves, respectively, the system.

Each leg may also include, for example, one or more proximity sensors to detect and/or measure the absolute or relative position of a vehicle as it passes through the frame. Such information may be used, for example to correct and/or optimize video images before analyzing for dents, dings, scratches, blemishes, or other anomalies. Such correction or pre-processing of video images may be of particular use, for example, to standardize the size of objects in the image to enable detection of damage or anomalies by comparison of symmetrical images of the vehicle (e.g., left versus right sides of the vehicle). In some embodiments, other light sources may be incorporated to provide more uniform light (e.g., not banded or striped light) to provide cleaner overall images of a vehicle. In some embodiments, an operator or user may select a desired light mode (and/or intensity) depending upon the desired application. In some embodiments, a custom lighting array utilizing light emitting diode (LED) light strips may fully illuminate a car and also provide a reflection that is used to specifically highlight dents.

In some embodiments the system may include a controller or system computer for controlling overall operation of the system components, including lights, cameras, and sensors. Such controller may have a CPU and memory including software programs or instructions for recording images, collecting data, processing data, analyzing data, communicating with a vehicle (or a transceiver within the vehicle), creating reports, and/or transmitting data over the Internet or other network to a central computer or server. In some embodiments, each leg and cross member of the system frame may include a pod unit with a group of cameras, sensor(s), and one or more video collectors or controllers for collecting and/or processing data and/or controlling components within each pod. In some embodiments, each pod communicates with a main ARC unit computer for overall control of the system.

In some embodiments, a vehicle imaging system may include a frame having a central passage configured and dimensioned to allow a vehicle to pass through the central passage, a plurality of cameras disposed within the frame and directed to record images of a vehicle passing through the passage, one or more sensors disposed within the frame, a light source integrated within the frame for illuminating the passage, and a controller, or computer, disposed within the frame for controlling the cameras, the sensors, and the light source. In some embodiments, the one or more sensors may include a proximity sensor for determining a distance of the vehicle with respect to the frame, a trip sensor for alerting the system to the entry or exit of a vehicle into the system, and/or a motion detector for detecting the presence of a vehicle or other object near the system. In some embodiments, the light source further comprises one or more lighting array panels comprising a plurality of elongated and substantially parallel LED channels for emitting an array of substantially parallel bands of light towards the central passage of the frame. In some embodiments, a base plate spanning between legs of the frame may include a plurality of substantially parallel bands of reflective material corresponding to the plurality of elongated and substantially parallel LED channels in the frame.

In some embodiments, a vehicle imaging system may further include a pair of front bollards positioned on a front side of the frame and a pair of rear bollards positioned on a rear side of the frame, wherein at least one of the front bollards and at least one of the rear bollards each includes a bollard camera directed toward the passage of the frame. The distance between bollards in each of the front pair and the rear pair may be less than or equal to a width of the passage between the legs of the system frame. Each pair of bollards may include one or more bollard sensors, for example a trip sensor configured for detecting an object passing between the two bollards in each of the front pair and the rear pair of bollards. In some embodiments, each leg of the frame may include a pod having two or more cameras, at least one sensor, and a video collector for collecting data from the two or more cameras and the sensor(s).

In some embodiments, the system incorporates a motion detector in communication with the system controller, wherein the motion detector is configured to detect the presence of an object near the frame, and the controller includes instructions for activating the plurality of cameras and the light source in response to a signal from the motion detector.

In some embodiments, the system controller may include a vehicle interface configured to wirelessly communicate with a wireless transceiver in the vehicle to receive and store vehicle identification and diagnostic information, such as, for example, any of the vehicle identification number, gas mileage, volume of fuel, engine codes, or GPS information obtained from an OBD II port on the vehicle.

In some embodiments, a method of detecting damage to a vehicle may include providing an apparatus having a frame surrounding a passage through which a vehicle may pass, said apparatus housing a plurality of cameras, a proximity sensor, and a lighting array configured to illuminate the passage; illuminating the passage using the lighting array; recording video of the vehicle using the cameras as the vehicle passes through the passage; recording position data indicating a position of the vehicle relative to the frame using the proximity sensor; processing the video and position data to adjust the size of images in the video to correct for variations in the position of the vehicle; and analyzing the processed video to detect anomalies in the vehicle.

In some embodiments, recording video may include recording simultaneous video images of the right side of the vehicle and of the left side of the vehicle. Analyzing the processed video may include comparing the video images of the right side of the vehicle with the video images of the left side of the vehicle to detect the anomalies. Such analyzing step may further include synchronizing and simultaneously presenting the video images of the right sight of the vehicle and video images of the left side of the vehicle over a network to an analyst to detect and flag the anomalies.

In such methods, the lighting array may include a panel having plurality of elongated and substantially parallel LED lights separated by dark bands to illuminate the vehicle with a striped light pattern to facilitate detection of the anomalies. The apparatus may also include a motion detector, and the method may further include the step of receiving an activation signal from the motion detector before illuminating the passage or activating the cameras. The apparatus used in such methods may further include a pair of front bollards on a front side of the frame and pair or rear bollards on a side of the frame opposite the front bollards, wherein recording video may further include capturing images from cameras housed within the front and rear bollards.

In some embodiments, data generated, or recorded by the system may be accessible through an intuitive user interface, e.g., for smart phones, tablets, laptops and desktop computers.

In some embodiments, the scanning apparatus or frame is configured and dimensioned to accommodate semi trucks and/or other tall vehicles, but the apparatus footprint is minimal. In some embodiments, a scanning apparatus and associated system components may be configured and dimensioned for easy assembly and installation.

In some embodiments, vehicle scanning systems described herein are fast, efficient and reliable so as not to impede the operations of the facility where the system is installed, including for example car dealerships, auction houses, rental car companies or rental car lots, body shops, and auto service centers. In some embodiments, a multi-use scanner system may be installed for use by multiple businesses, e.g., a centrally located and operated pay-per-scan system may be shared by multiple car rental companies at an airport location, or for example by multiple auto repair companies at an auto service center, each with access to login to the system to view images and perform analyses.

In some embodiments, damage to a vehicle body may be determined by using a left side versus right side comparison of images. For example, using image data collected by the system, a car may be split down the middle, e.g., into symmetrical halves such that images and/or video of the right and left sides of the vehicle may be compared to determine damage such as dents, dings, scratches, blemishes or other asymmetrical anomalies.

These as well as other aspects and advantages will become apparent to those of ordinary skill in the art by reading the following detailed description, with reference where appropriate to the accompanying drawings. Further, it should be understood that the embodiments described in this overview and elsewhere are intended to be examples only and do not necessarily limit the scope of the invention.

BRIEF DESCRIPTION OF THE DRAWINGS

Example embodiments are described herein with reference to the drawings.

FIG. 4A a side view illustration viewed from the outside of a leg of the frame of the frame of FIG. 1 in accordance with an example embodiment.

FIG. 4B is an exploded view illustration viewed from the inside of the leg of FIG. 4A, showing components of the leg, electronics pod, and LED array panel in accordance with one or more example embodiments.

FIG. 5A is a cross sectional top view illustration of an assembled frame leg of FIG. 4B, taken through camera 328, in accordance with one or more example embodiments.

FIG. 5B is an expanded view of a portion of the LED array panel of FIG. 5A, in accordance with one or more example embodiments.

FIG. 6A is a top view of the base plate of the automated radial imaging system of FIG. 1, in accordance with one or more example embodiments.

FIG. 6B is a top view of the base plate of FIG. 6A, with an attached wheel guide and frame legs in accordance with one or more example embodiments.

Like reference numerals refer to the same or similar components throughout the several views of the drawings.

DETAILED DESCRIPTION

I. Overview

Described herein are systems and methods for imaging a vehicle and detecting vehicle damage. In the following description, for purposes of explanation, numerous examples and specific details are set forth in order to provide a thorough understanding of the invention. It will be evident, however, to one skilled in the art that the present invention may include some or all of the features in these examples alone or in combination with other features described below, and may further include modifications and equivalents of the features and concepts described herein.

II. Examples: Automated Radial Imaging System

Figure 1:
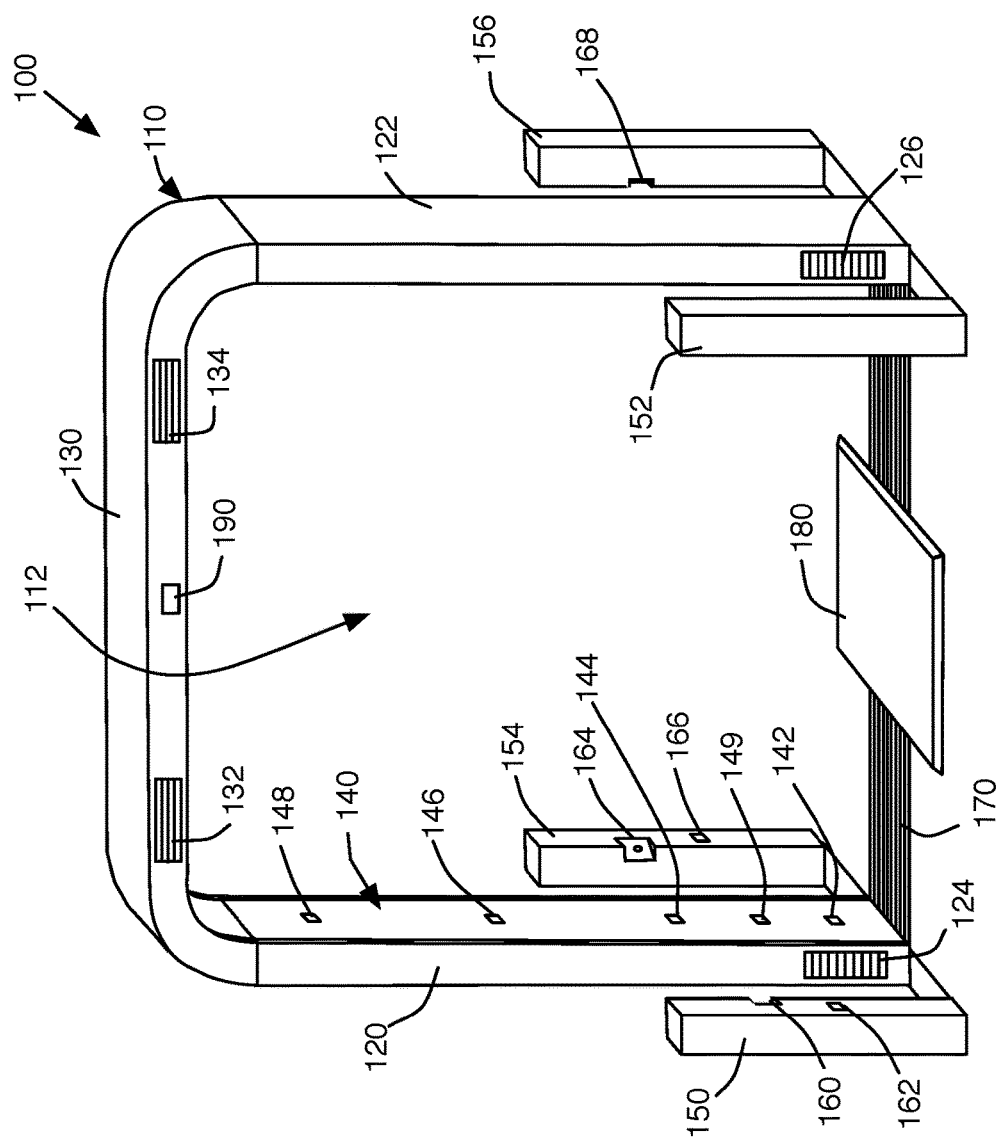
FIG. 1 is a perspective view illustration of an automated radial imaging system in accordance with one or more example embodiments.

Referring to FIG. 1, in some embodiments an automated radial imaging and analysis apparatus and system 100 (also referred to herein as an "automated radial cartography system", "ARC", or simply "system") may include an arched frame 110 having legs 120, 122 and a top 130 or cross member connecting the legs 120, 122 and forming a central passage 112. Passage 112 may be configured and dimensioned to accommodate the passage of a vehicle, e.g., an automobile, truck, motorcycle, boat, or other vehicle.

Each leg 120, 122 and top member 130 (also referred to herein as cross member 130) may also include a lighting array panel 140 forming an inner surface of the frame 110 and configured to emit light for illuminating a vehicle passing through the passage 112. In some embodiments, each panel 140 may include one or more camera windows 142, 144, 146, 148 and/or sensor windows 149 through which cameras, sensors, or other devices may detect, image or otherwise interact with a vehicle in the passage 112. In some embodiments, top member 130 may also include one or more sensors 190, e.g., a motion sensor 190 for use in detecting the presence of a vehicle to be scanned and/or for activation of the system 100. In some embodiments, sensor 190 may be a sensor configured to detect and/or distinguish large objects (e.g., vehicles) from smaller objects such as a person. In some embodiments, system 100 may incorporate multiple sensors 190 for detecting objects one or both sides of the system, and may incorporate or interface with a camera or other device to aid in distinguishing objects and/or activating/deactivating the system 100.

In some embodiments, frame 110 may house a number of different components, such as cameras, sensors, processors and/or computer systems for controlling the system and collecting and analyzing data, as shown and described in more detail herein. In some embodiments, frame 110 may include one or more vents 124, 126, 132, 134 to allow air flow through the frame, e.g., to maintain a desired operating temperature for components housed within the frame.

In some embodiments, system 100 may also include one or more bollards 150, 152, 154, 156, for example positioned a desired distance in front and back of each leg 120, 122. For example, in some embodiments, each bollard 150, 152, 154, 156 may be positioned 12 to 48 inches from the front and back side of each leg 120, 122. In other embodiments, each bollard may be positioned approximately 24 inches from each leg 120, 122. Various other bollard positions or combinations may be used without departing from the scope of the invention.

In some embodiments, each bollard 150, 152, 154, 156 may include one or more cameras 160, 164, 168 and/or one or more sensors 162, 166. For example, each camera 160, 164, 168 may be directed toward the ARC passage 112, e.g., to capture video and/or still images of the front and back of a vehicle passing through the passage 112. In the example system 100 of FIG. 1, front bollard 152 may include a camera and sensor, and rear bollard 156 may include a sensor, where each of which are not shown due to the perspective view of the figure. For example, in such an arrangement, as a vehicle passes through the ARC passage 112, sensors on one or more of the rear bollards 154, 156 (e.g., sensor 166) may detect the vehicle and/or position of the vehicle, e.g., to activate the system 100 and/or for collecting data for use in correcting images collected by cameras in the system. Also, one or more cameras in front bollards 150, 152 may be positioned and directed to collect video and/or still images of the rear of a vehicle passing vehicle through the ARC passage 112, while one or more cameras in rear bollards 154, 156 (e.g., cameras 164, 168) may be positioned and directed to collect video and/or still images of the front of the vehicle.

In some embodiments, cameras in front bollards 150, 152 and/or rear bollards 154, 156 may be used to provide vehicle identification information, e.g., from an image of the vehicle license plate, bar code, auction number, or other indicia on the vehicle. Image recognition software in the system (e.g., in controller 450 of FIG. 4 or in a remote or central server 860 of FIG. 8) may be used to analyze images of license plates, codes, or other indicia to obtain vehicle information to be associated with the vehicle imaging records. In some embodiments, one or more sensors in bollards 150, 152, 154, 156 or in frame 110 may include bar code readers, RFID readers or other sensors for obtaining vehicle identification information and/or other vehicle data.

In some embodiments, a base plate 170 spans between legs 120 and 122. Plate 170 may include an array of substantially parallel stripes, e.g., alternating light and dark stripes. In some embodiments, the light stripes may be white, silver, metallic, or other reflective color or material, while dark stripes may be black or other dark color. In an example of use, when light from light panels (e.g., panel 140) in legs 120, 122 and top member 130 strikes base plate 170, light may be substantially reflected by the light stripes and absorbed by the dark stripes, such that substantially parallel stripes or lines of light are reflected upward onto a vehicle to aid in detecting damage or defects in the lower portion of the body of the vehicle.

In some embodiments, a guide 180, may be positioned over base plate to aid in the positioning of wheels of a vehicle as it drives through the ARC 100 to be scanned or imaged. For example, guide may be configured and dimensioned to have a width that is less than the wheel base of most vehicles, e.g., in some embodiments between 30 inches and 60 inches, or as otherwise appropriate for the desired application. Guide 180 may also have a height, e.g., 1 inch to 4 inches, or as otherwise desired, to serve as a curb or other obstacle for wheels to drive over, for example to help guide the positioning of a 4-wheeled vehicle (e.g., a car, truck, or trailer) such that the guide 180 is positioned between the right and left wheels of the vehicle. In some embodiments, one or more edges of guide 180 may be rounded or beveled as shown in FIG. 1.

Figure 2B:
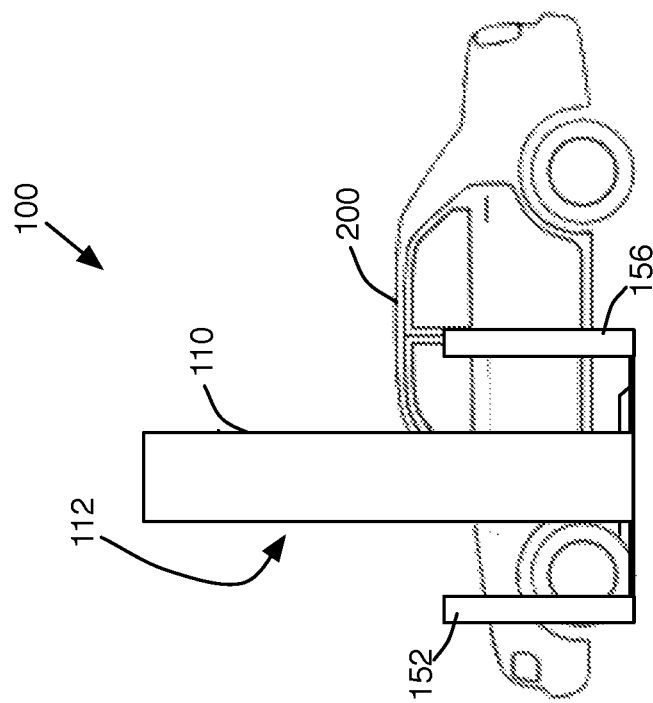
FIG. 2B is a side view of the example system and automobile of FIG. 2A.
Figure 2A:
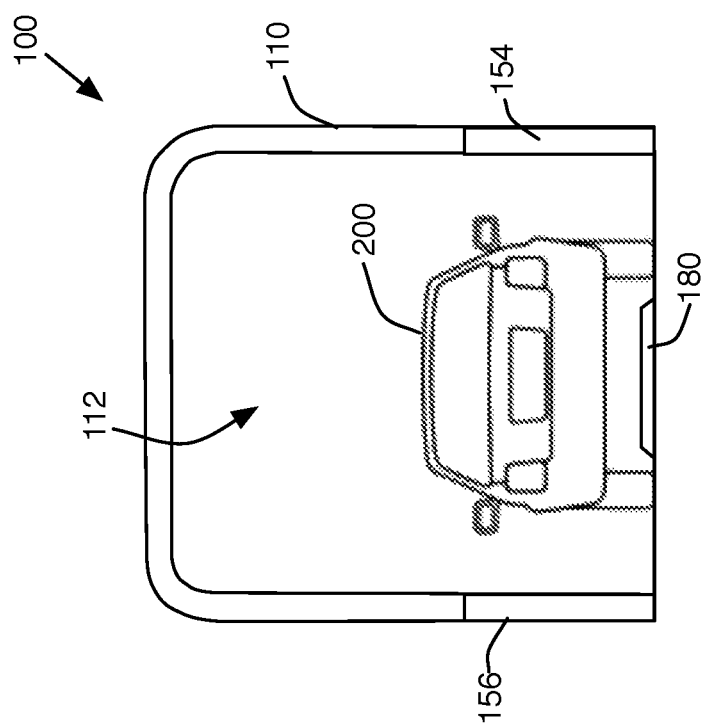
FIG. 2A is a rear view of the system of FIG. 1 in use for scanning an automobile in accordance with one or more example embodiments.

FIGS. 2A and 2B show a basic example of using system 100 with an automobile 200, or car, positioned or moving through the central passage. FIG. 2A is a rear view, showing vehicle 200, positioned over guide 180 and between rear bollards 154, 156 as it moves through the central passage 112 of frame 110.

FIG. 2B is a side view of the system 100 and vehicle 200 of FIG. 2A. As vehicle 200 drives into the ARC 100, motion detectors in one or more of the rear bollards 154, 156 may detect to the vehicle and activate the system, e.g., to illuminate the light panels in the frame 110 and begin recording video from cameras in the frame 110 and front bollards 150 (from FIG. 1), 152 and rear bollards 154, 156.

Figure 3:
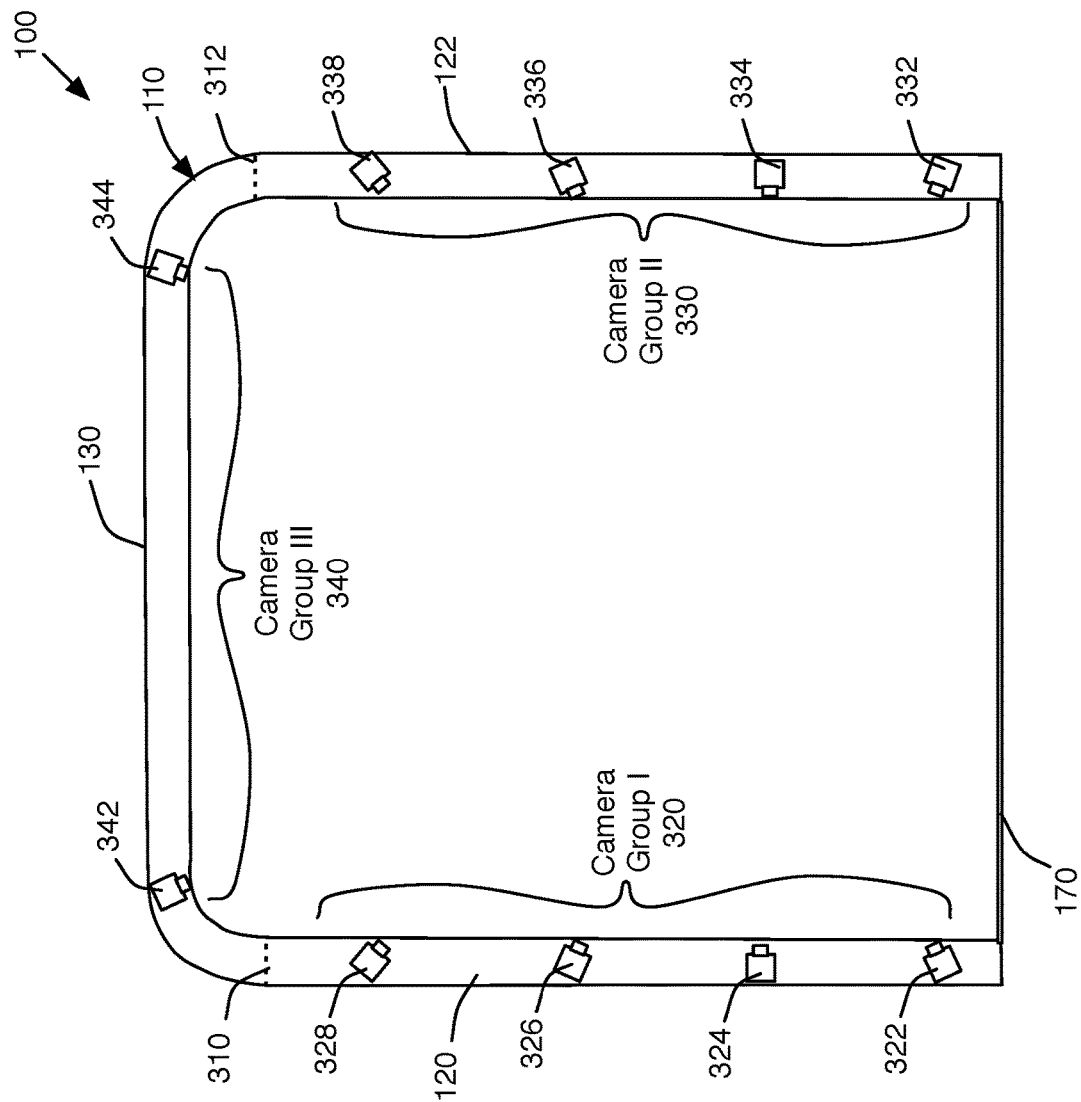
FIG. 3 is a schematic front view illustration of the system of FIG. 1 showing approximate placement of cameras within the legs and top member of the frame of the scanner in accordance with one or more example embodiments.

Turning now to FIG. 3, one or more cameras may be positioned in each leg 120, 122 and in top member 130 (shown schematically for purposes of explanation). In some embodiments, cameras may be grouped into functional units or groups. For example cameras 322, 324, 326, 328 in leg 120 may be in a group, e.g., "camera group I" 320. Similarly, cameras 332, 334, 336, 338 may be in another group, e.g. "camera group II" 330. In this example, two top cameras 342, 344, may be grouped as "camera group III". Not shown in this figure, cameras in each bollard 150, 152, 154, 156 may be grouped in a fourth group, e.g., "camera group IV". The cameras may be positioned within frame 110 and directed at desired angles to capture video and/or still images of all sides of a vehicle driving through the system 100, e.g., with camera group 320 in leg 120 positioned for imaging the right side (including top bottom edges) of the vehicle, camera group 330 in leg 122 positioned for imaging the left side (including top and bottom edges) of the vehicle, and camera group 340 in top 130 member positioned for imaging the top of the vehicle. Similarly, cameras in bollards 150, 152, 154, 156 of FIG. 1 may be positioned and directed to provide images of the right front, left front, right rear, and left rear, respectively, of the vehicle. Each group may be associated with one or more processor, video collectors, and/or other components as described in additional examples below, e.g., to facilitate control of cameras and collection and processing of images.

In some embodiments, cameras of groups 320, 330, 340, and/or those in bollards 150, 152, 154, 156 may be any desired type of video and/or still cameras, for example high definition (HD) CCD or CMOS video cameras, high dynamic range (HDR) cameras, or other small cameras or camera systems capable of capturing video images of sufficient quality, frame rate and resolution to detect defects or deformities in a vehicle. In some embodiments, cameras of each group 320, 330, 340, and/or those in bollards 150, 152, 154, 156, may interface with one or more camera controllers, video collectors, frame grabbers, and/or machine vision hardware and/or software for collecting, processing and/or analyzing images.

Turning now to FIGS. 4A and 4B, additional examples of components of system 100 are shown. FIG. 4A is a side view of frame 110, showing the outside of leg 120 and top member 130. In some embodiments, top 130 and leg 120 are secured together at a joint 310. In other embodiments, frame 110 may be constructed of multiple sections. In other embodiments, frame 110 may be constructed of a single section.

FIG. 4B shows an exemplary exploded view of leg 120 taken from the central passage of the system 100, showing example structural elements and electronic and lighting components in accordance with an example embodiment. Top 130 member of frame 110 is shown in cross-section in this figure, illustrating structural features of frame 110 such as curved edges 412 and a central hat channel 410 running the length of the interior of each section of the frame. In some embodiments, frame may be constructed of aluminum, steel, alloy, fiberglass, plastic, composite, polymer, glass, or other material or combination of materials. Edges 412 and hat channel 410 may help provide structural integrity for the frame 110 to prevent bowing or bending of the frame and to house and protect internal components. In some embodiments, a mounting plate 340, e.g., made of steel or other desired material, together with one or more fasteners 432, may be used to secure frame to a the ground, e.g., to a concrete floor or paved driveway. In some embodiments, a mounting plate 340 is positioned at each end of a base plate (e.g., base plate 170 of FIG. 1). In other embodiments, any suitable means of anchoring or securing the frame in position may be employed.

In some embodiments, one or more guides or tabs 422, 424, e.g., welded or secured to top end of leg 120 and/or corresponding bottom end of cross member 130 may be used to position and align and secure the legs and cross member during assembly. One or more couplers 420, e.g., straps, brackets, or other devices, may also be used (e.g., in addition to or instead of tabs 422, 424) to secure adjacent structural components. In this example, coupler 420 may be bolted to hat channel. In some embodiments, a bar, strap, coupler or other member may be disposed within hat channel 410 (e.g., behind coupler 420) to additional support for joining components. In some embodiments, one or more structural components may be welded, bolted, riveted, or otherwise secured together to provide desired structural integrity for the frame 110 and/or other components.

In some embodiments, frame 110 is configured and dimensioned to house components such as one or more units or pods 400, each of which may include a board 440 supporting one or more cameras 322, 324, 326, 328 and associated components such as a video collector 460 for collecting videos from cameras on the pod and/or corresponding camera group. Pod 400 may also include one or more sensors 452, e.g., a motion detector, proximity sensor, and/or other sensor. One or more connectors 456 may be used to connect adjacent pods and/or lighting panel 140, e.g., to provide power, data, instructions and/or other communications between pods. In some embodiments, video collector 460 may be a computer (e.g., including a processor and memory with applications or instructions) for collecting and/or aggregating data from corresponding cameras, sensors and other components associated with the pod 400 or functional group. In some embodiments, collector 460 may include a frame grabber or other applications or instructions for collecting selected frames of recorded video.

Figure 8:
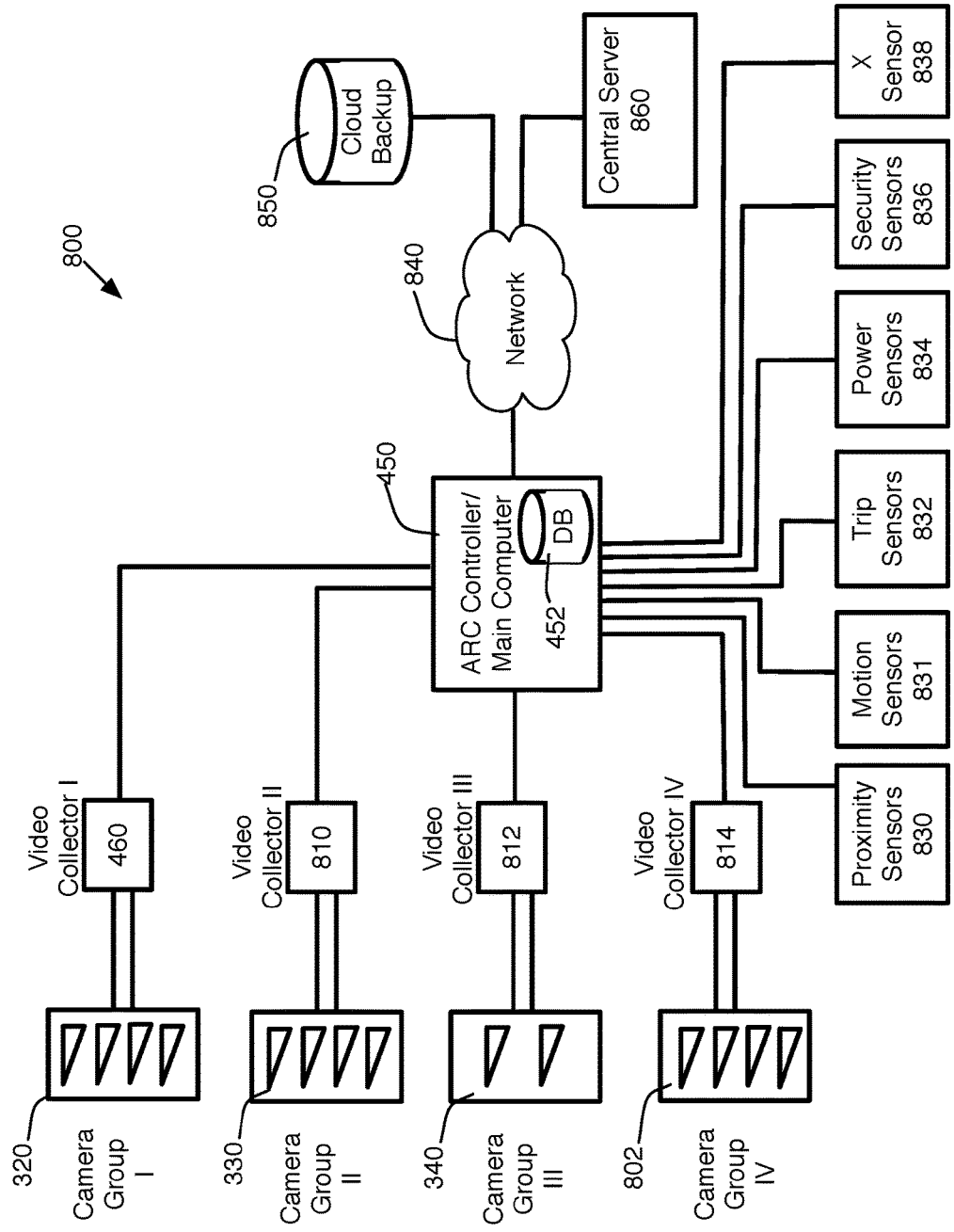
FIG. 8 is a schematic diagram of an automated radial imaging system in accordance with one or more example embodiments.
Figure 9:
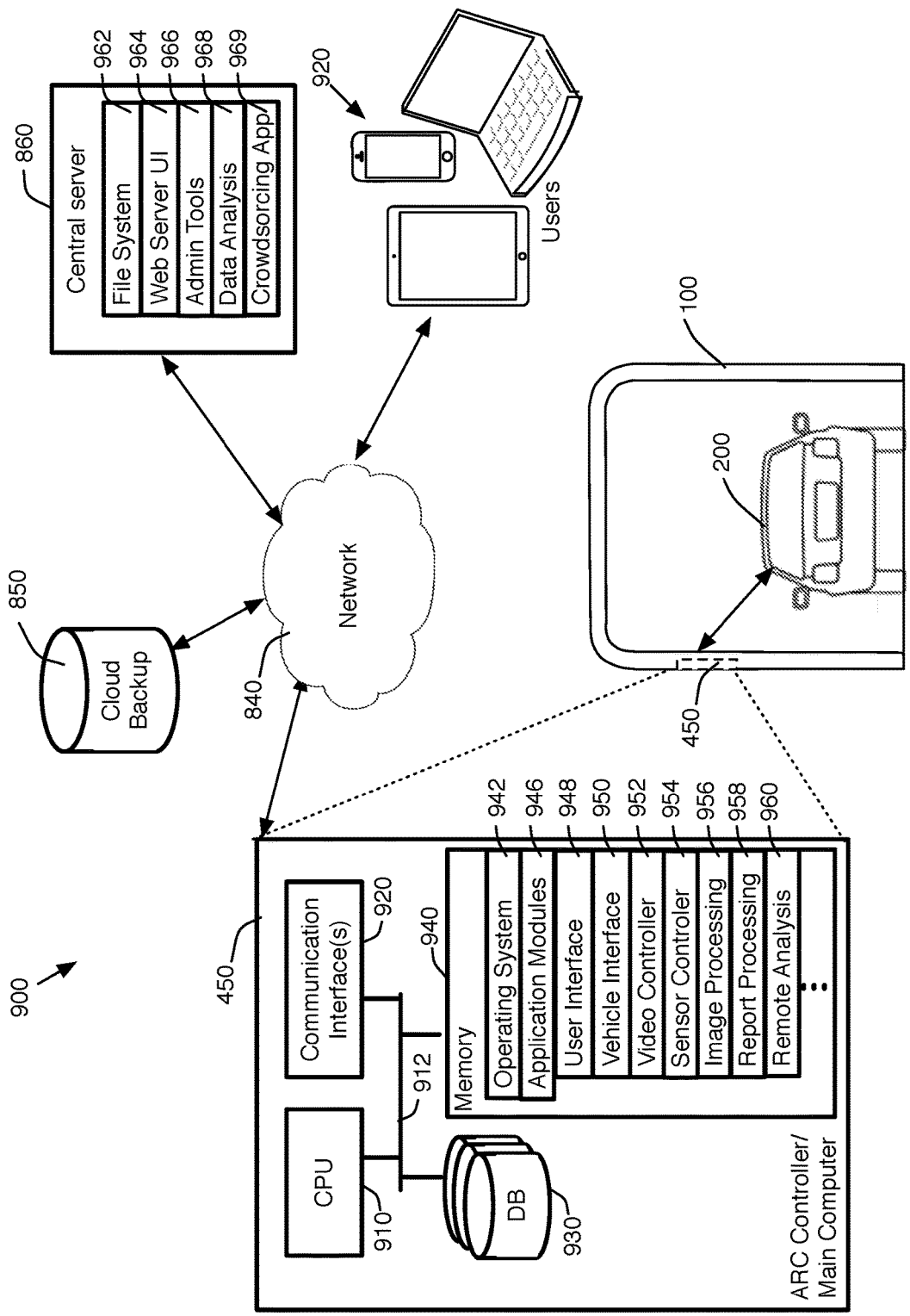
FIG. 9 is another schematic diagram of an automated radial imaging system and network in accordance with one or more example embodiments.

In some embodiments, system 100 may include one or more main computers, processors, or servers, referred to herein as system controller 450 (or "main computer", or "ARC controller" in FIGS. 8 and 9). System controller 450 may provide overall control of the ARC system 100, including control of cameras, sensors, lighting, and communication between components within frame 110 and/or the bollards. Controller 450 may also include one or more communication interfaces, e.g., to communicate with sensors or devices within a vehicle (e.g., to obtain vehicle information) and/or to communicate over a wired or wireless network (e.g., such as the Internet, cellular network and/or local area network), for example with a central server, cloud servers, databases, client systems, administrators and/or user devices (e.g., computers, laptops, and mobile devices).

In the example embodiment of FIG. 4B, controller 450 is located on pod 400 of leg 120 and is electronically coupled directly or indirectly with each electronic component of the system, including for example components on pod 400 as well as those in corresponding pods within leg 122 and top member 130, and components within each bollard. In some embodiments, one or more power supplies 454 may be used to provide power to controller 450 and other components within the system 100. In some embodiments, board 440 may be any suitable board, substrate, or other structural member for mounting the various electronic components of pod and may comprise, for example, one or more printed circuit boards to provide structure and communication between components.

In some embodiments, leg 120 (as well as leg 120 and top member 130) will have an associated lighting array panel 140 that is configured and dimensioned to secure to the leg and cover pod 400, e.g., electrically connected to pod 400 and controller 450 through a connector such as connector 456. In some embodiments, each panel 140 may include a plurality of substantially linear and parallel light bands or strips 172 separated by black, dark, or otherwise non-illuminated strips such that light emanating from the panel 140 appears as substantially parallel stripes of light. In some embodiments, one or more windows 142, 144, 146, 148 may provide openings for corresponding cameras 322, 324, 326, 328, respectively, and window 149 may provide an opening for sensor 452 to send or receive signals for detecting proximity or distance of a vehicle from the leg 120 (e.g., using electromagnetic field, light, sound, or other signals). In some embodiments, other types of sensors may be employed. In some embodiments, panels 140 or other light source devices may be configured to provide desired patterns of structured light to facilitate dent detection. In some embodiments, leg 120 may include lights, lasers, sensors, and/or other components for 3D scanning of a vehicle, for example to detect dent, dings or other anomalies, or in some embodiments to create an image or 3D model of the vehicle.

One skilled in the art will appreciate that the arrangement and connection of components shown in FIG. 4B are examples only, and other components and arrangements may be employed without departing from the scope of the claims. For example, the interconnection of components may be arranged as desired for optimal communication between components and/or with one or more processing units or controllers; and/or one or more cameras or sensors may be integrated within or mounted over lighting components.

Turning now to FIGS. 5A and 5B, additional details of structural and electronic components are shown in accordance with one or more example embodiments. FIG. 5A is a top cross-sectional view of leg 120 and associated components from FIG. 4B, taken through line 5B at camera 328. Frame 110 is shown having edges 412 and hat channel 410, which may provide structural support for the overall system 100 and a substrate for mounting components such as pods 400. Frame may also include one or more brackets 510, which may be secured to or integrated with the inner surface of the frame, and which may provide additional support and mounting surfaces for board 440 of pod 400 and/or other components of the system.

In this example, board 440 of pod 400 provides a substrate for components of the pod 400, including for example processor 450, camera 328, and other components. One or more cables or wires 530, and/or in some embodiments fiber optic cables and/or printed circuits, may be used to provide power and/or for communication of between components. Lighting array panel 140 is also shown in cross section in FIG. 5A, secured to frame over pod 400 in this example and spanning the distance between outer edges 412 of frame 110. Panel may include an array of light strips 472 for emanating lines of light toward a vehicle moving through or positioned within the ARC system 100.

FIG. 5B is an expanded, close up view of LED panel and three light strips 472. In this embodiment, light strips 472 are configured as LED reflector channels (also referred to herein as "channels 472"), each housing a linear LED light 560 and having angled reflectors 552, 554 for reflecting and directing light from the LED 560 outward from the panel 140. Disposed between each LED channel 472 may be a black or dark strip 556, e.g. configured and dimensioned to provide contrast between adjacent 472 such that light emanating from the array of channels 472 is projected as an elongated array of parallel stripes of light. A cover 540, e.g., of glass, acrylic, polycarbonate or other transparent or semi-transparent material may be used to cover and protect the light channels 472, e.g., for ease of cleaning and/or optimizing the properties of light emitted from the panel 140. In some embodiments, cover 540 may be frosted, colored, or otherwise treated to diffuse or filter light.

In some embodiments, other lighting configurations may be employed. For example, cover 540 may be configured as a lens having dark or opaque barriers or strips integrated within or affixed to cover 540, e.g., to provide striping or other patterned effect of light emanating from the panel. In some embodiments, lighting panels may be configured to emanate light in other patterns, or no pattern, depending upon the desired application. For example, in some embodiments, bright, diffuse light may be used for uniform illumination of a vehicle for video recording of the features of the vehicle a vehicle, as opposed to using stripes for aiding in detection of dents, dings, or other irregularities in the body of a vehicle as described herein.

FIGS. 6A and 6B are top views of a base plate 170 and associated components in accordance with one or more example embodiments. FIG. 6A shows a base plate before attachment of legs 120, 122 and guide 180. In this example, plate 170 may include a plurality of substantially parallel reflective (e.g., white, silver, metallic, or other reflective color or material) stripes 610 separated by dark or opaque areas 612 to provide contrast between the reflective stripes. In some embodiments, the array of stripes 610 correspond to the stripes from LED panels 140 and help reflect a striped light pattern from the base of the ARC system 100 to aid in detecting dents, dings, or other deformities in the body of an automobile.

In some embodiments, one or more mounting plates 620, 630 may be used to secure the bottom end of legs 120, 122. Each mounting plate may secure to the floor or other surface (e.g., a concrete or asphalt drive), by fasteners 632 such as bolts or other fastening devices. In some embodiments, each mounting plate may include one or more flanges 624, 634, blocks, angle brackets, or other devices the extend upward from the mounting plate 620, 630, e.g., to facilitate securing of each leg 120, 122, to each mounting plate. In some embodiments, base plate 170 may include one or more guide mounts 640 or holes for positioning and securing guide 180 over the base plate 170 and/or securing base plate to the ground. In some embodiments, base plate 170 may be embedded in concrete or asphalt, e.g., to help secure the base plate 170 and avoid damage or wear as cars drive through the apparatus.

FIG. 6B shows a top view of the base plate of FIG. 6A, with legs 120, 122 and guide 120 mounted in their respective positions. As described above, each leg 120, 122 may include one or more electronics pods 400, 400' and LED array panels 470, 470'. In some embodiments, guide 180 may include arrows 680 or other indicia to indicate a desired direction of passage of a vehicle through the system. In some embodiments, the system 100 may be configured as a bi-directional system, such that a vehicle may pass in either direction, and the electronics pods 400, 400' may record images, sensor data, and other data associated with the vehicle in accordance with the direction of travel.

In the embodiment of FIG. 6B, guide 180 is shown as a rectangular curb device having beveled edges to discourage but allow passage of tires over the guide 180. In some embodiments, other guide configurations or devices may be employed, such as wheel channels, rails, barriers, or other devices to help optimize positioning of a vehicle within the ARC system 100. In some embodiments, the width, length, height, shape, position or orientation of one or more guides may be adjusted, and/or different guide configurations (or no guide) may be used depending upon the desired application.

In some embodiments, an ARC frame 110, with or without bollards, base plate, and/or guide, may be configured to move linearly, e.g., on a track or on wheels, over a stationary vehicle rather than have the vehicle drive or otherwise move through the frame passage. Such embodiments may be useful in an environment where vehicles sometimes cannot move under their own power, e.g., in a body shop environment. In some embodiments, wheel guides, tracks, pulleys, or other devices may be employed to push or pull a non-operational vehicle through the scanner.

Figure 7B:
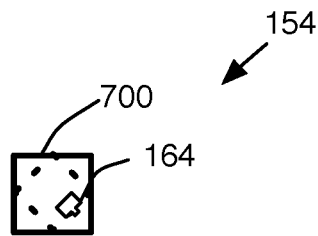
FIG. 7B is a top view of the example bollard of FIG. 7A.
Figure 7A:
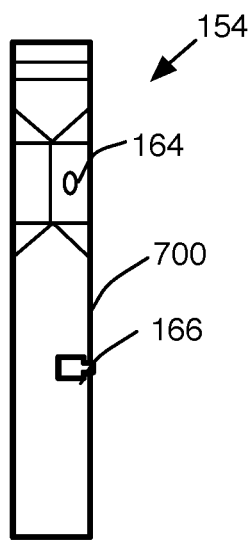
FIG. 7A is a side view of a bollard having a camera and a vehicle sensor in accordance with an example embodiment.

Turning now to FIGS. 7A and 7B, side and top views, respectively, of an example bollard 154 are shown in accordance with one or more example embodiments. Bollard 154 may have a body 700 of any desired size or shape, e.g., in this example approximately 4 to 8 inches square from a top view (FIG. 7B) and approximately 2 to 6 feet, or in some embodiments 3 to 5 feet, in height above ground. In some embodiments, each bollard 154 may be anchored or embedded in the ground, e.g., 1 to 3 feet deep or any other desired depth, to help maintain position of the bollard and/or provide protection from a vehicle striking the main frame 110 of the system (e.g., as shown in FIG. 1). In some embodiments, one or more bollards 154 may be connected to the frame 110 or mounting plate, e.g., by a plate secured to mounting plate 620 or 630 of FIG. 6.

In some embodiments, bollard 154 may include, for example, camera 164 and one or more vehicle sensors 166, e.g., a motion sensor, safety sensor, proximity sensor, or other sensor or device. In some embodiments, camera 164 may be positioned within the bollard and directed to provide an image or video of a front or rear portion of a vehicle passing through the system 100, e.g., to detect damage on the rear of the vehicle, provide an image of the vehicle license plate, or other desired image. Similarly, each sensor 166 may be oriented in any desired direction depending upon the application, or the event or object to be sensed.

The foregoing description and corresponding figures are intended to illustrate various features of example embodiments of an exemplary ARC System 100, and one skilled in the art will appreciate that various other features, components, aspects, materials, and arrangements may be employed.

III. Example Architecture

Turning now to FIG. 8, an example control system 800 for an ARC apparatus may include a central ARC controller/server 450 (also referred to herein simply as "controller 450"), which may be configured as an on-board computer system, e.g., having a CPU, communication interfaces, bus, database, memory, and software instructions for overall control and operation of the system, as described in more detail below with respect to FIG. 9. Controller 450 may communicate directly or indirectly with one or more video cameras or camera groups, for example, camera group I 320 for cameras in leg 120 of FIG. 1, camera group II 330 for cameras in leg 122, camera group III 340 for cameras in cross member 130, and camera group 802 for cameras in bollards 150, 152, 154, 156. Each camera group 320, 330, 340, 802 may be associated with a video collector 460, 810, 812, 814, respectively, for collecting video from the corresponding camera group and communicating with the controller to process and/or store the collected images. Images and other information about scanned vehicles may be stored in a database 452 associated with the ARC controller 452.

In some embodiments, controller 452 may also communicate with one or more sensors associated with the system 100, for example one or more proximity sensors 830, safety beam sensors 832, power sensors 834, security sensors 836, or other configurable sensors 838. In some embodiments, one or more proximity sensors may be housed, for example, in a frame of an ARC apparatus (e.g., sensor 452 of FIG. 4), and may detect the presence of a vehicle and/or measure the distance of the car from each leg of the frame or a bollard. In some embodiments, such measurements may be used to adjust or correct for the position of the vehicle when analyzing video data, e.g., when comparing video taken of one side of the vehicle to that taken of the other side.

In some embodiments, one or more safety beam sensors 832 may be housed, for example, in one or more bollards and/or in the frame of the system. Such sensors 832 may be used, for example, to sense the presence of a vehicle, a person, or other object, and to activate, deactivate, pause, or initiate some other action on the system in response to the detected object. For example, in some embodiments, one or more bollards in front of or behind an ARC frame may have one or more motion detectors, e.g., large object scatter beam detectors or other detectors for detecting large or small objects.

In some embodiments, one or more power sensors 834 may be used to monitor and/or control power to the 800 system and/or its various components.

In some embodiments, one or more security sensors 836 may be used to monitor various components of the system to ensure proper operation, and/or monitor access to the system, e.g., to prevent tampering or unauthorized access. In such embodiments, activation of a security sensor 836 may activate an alarm or other alert system, and/or may shut down the system or perform another desired action configured within the controller 450.

In some embodiments, controller 450 may be configured to communicate with and/or control one or more other sensors 838 or devices associated with the system, e.g., sensors for environmental conditions (e.g., temperature). In some embodiments, controller 450, e.g., through a sensor 838 or other device, may communicate with a drone, micro camera, handheld device, or other remote sensor or camera system, e.g., to record video or other images of the interior of a vehicle, and in some embodiments to associated those images with recorded vehicle data and/or images taken by the camera groups 320, 330, 340, 802.

In some embodiments, ARC controller 450 may communicate over a network 840, e.g., the Internet or other network, with other devices such as external databases or backup systems 850 and/or one or more computer systems 860 (also referred to herein as "server 860"). The computer system 860 represents a generic platform that includes components that may be in a server or another computer system. The computer system 860 may be a single system or server, a distributed system, or one or more cloud services. The computer system 860 may execute, by a processor or other hardware processing circuit, the methods, functions and other processes described herein. These methods, functions and other processes may be embodied as machine readable instructions stored on computer readable medium, which may be non-transitory, such as hardware storage devices (e.g., RAM (random access memory), ROM (read only memory), EPROM (erasable, programmable ROM), EEPROM (electrically erasable, programmable ROM), hard drives, and flash memory).

In some embodiments, the one or more servers 860 may be used to configure the system 800 and/or to collect recorded vehicle or system 800 data, to analyze images, or perform other remote operation or analyses of the system and/or data. In some embodiments, server 860 and/or cloud backup 850 may include a database of vehicle records, e.g., images and/or data records associated with previously-scanned vehicles and/or various makes and models of vehicles. In some embodiments, server 860 may include hardware and/or software for video analysis and/or editing, e.g., for automated or human analysis or playback of recorded video, for analysis of detected damage, creation or manipulation of records, etc.

Turning now to FIG. 9, another schematic view of an example system architecture 900 is shown, with ARC controller 450 housed in an ARC apparatus 100. In some embodiments, ARC controller 450, or computer, may include a central processing unit, or CPU 910, communicating over a bus 912 with one or more components, such as a communication interface 920, one or more databases 930, and a memory 940 or other computer-readable medium for storing various programs or instructions. For example, memory 940 may include an operating system 942 for controlling overall operation of the controller and/or system 100 and one or more application modules 946.

In some embodiments, application modules may include a user interface 948, vehicle interface 950, video controller 952, sensor controller 954, image processing 956, report processing 958, and/or one or more remote analysis applications 960.

In some embodiments, user interface module 948 may include instructions, screen and/or data for a user 920 and or central server 860 to interface with the system 100, e.g., for configuring features of the system, accessing reports, viewing video and/or vehicle records, analyzing data, etc. In some embodiments, user interface 948 is an administrator interface, e.g., for configuring features of the system computer 450. In some embodiments, an administrator may access data, records, and/or configure various features and parameters and features of system computer 450, e.g., using administration tools 966 of central server 860.

In some embodiments, controller 450 may communicate with a vehicle 200, e.g., through a vehicle interface 950, which may include or be associated with a wireless interface (e.g., Wi-Fi, Bluetooth, radio frequency, cellular, or any other desired communication protocol or combination of protocols) configured to send and/or receive signals and/or data with a transceiver or other device in a vehicle passing through the ARC apparatus 100, e.g., to obtain vehicle identification and/or diagnostic information. Examples of vehicle on-board diagnostic communication devices and methods are described in more detail below with respect to FIGS. 10A, 10B, and 10C.

In some embodiments, a video controller 952 may communicate with one or more video cameras and/or video collectors of system 100 to control the operation of the cameras and/or the collection of video and/or still images. For example, video controller 952 may communicate with one or more video collectors 460, 810, 812, 814 (of FIG. 8) to collect and/or control the collection of video images, and/or controller 952 may communicate directly or indirectly with one or more cameras or camera groups 320, 330, 340, 802 (of FIG. 8) to control the associated cameras or camera groups.

In some embodiments, sensor controller 954 may control one or more sensors of an ARC system 100, e.g., motion detectors, proximity sensors, or other sensors. For example, sensor controller 954 may be configured to interface with, monitor and/or control proximity sensors 830, safety beam sensors 832, power sensors 834, security sensors 836 and or other sensors 838 of FIG. 8.

In some embodiments, image processing module 956 may be configured to process images collected from cameras associate with system 100. In some embodiments, image processing module 956 may provide real-time analysis of images of a vehicle 200, e.g., to detect damage such as a ding, dent, or scratch, and/or to flag suspicious or anomalous features. In some embodiments, module 956 may be configured to analyze recorded images or data, e.g., from database 930 or from backup data 850 over network and/or from data stored in one or more central or remote file servers, e.g., server 860.

In some embodiments, one or more report processing modules 958 may be configured to produce, manipulate, and/or provide reports of vehicle data recorded and/or processed by the system 100. For example, such reports may include information regarding damage or deformities detected by the system, vehicle identification and/or diagnostic information gathered from vehicle interface 950, vehicle history information, or other desired information or data.

In some embodiments, one or more applications 960 may be configured for users 920 and/or administrators via server 860 to access video images and/or records, e.g., to perform remote analysis of vehicle images captured by the system 100 and/or stored locally in system computer 450.

In some embodiments, central server 860 may include several modules for interfacing with one or more ARC system computers 450 and/or for storing, serving, and analyzing data collected and/or processed by one or more ARC systems 100. For example, server 860 may include one or more of a file system 962, a web server UI 964, administration tools 966, data analysis module 968, and/or image analysis modules 969 such as a crowdsourcing application (or "app") for presenting processed video to authorized users for analysis.

In some embodiments, data generated, or recorded by the system may be accessible through an intuitive user interface, e.g., web server UI 964, which may be configured for access and use by smart phones, tablets, laptops and desktop computers.

In some embodiments, video recorded from the right and left sides of a vehicle may be presented or streamed (or in some embodiments, uploaded or downloaded) over the Internet 840 to a user 920 of a crowdsourcing app 969. In such embodiments, one or more users 920 of the app 969 may visually compare the video to detect and/or flag potential damage or deformities and/or to report findings. For example, simultaneous side-by-side streams of the right and left sides of a vehicle may be provided and compared by the analyst to look for anomalies, e.g., indicated by a difference between the two streams. In some embodiments, the vertical banding of light provided by the lighting array panels 140, 470 may aid in detection of anomalies, e.g., by sudden movements or variations in the shape or distance between adjacent bands as the vehicle passes by. In some embodiments, the computer 860, or the app 969 may be used to overlay images to aid in detecting differences and/or anomalies between otherwise symmetrical sides of a vehicle.

In some embodiments, the app 969 may manage users 920 (e.g., with user accounts and configurable account access) and/or track usage and manage compensation for users who provide remote analysis services. In some embodiments, determinations of analysts may be stored or recorded by the application 969 to be used for teaching the system and developing a machine-learning module for automated analysis of video images to detect damage.

Figure 10C:
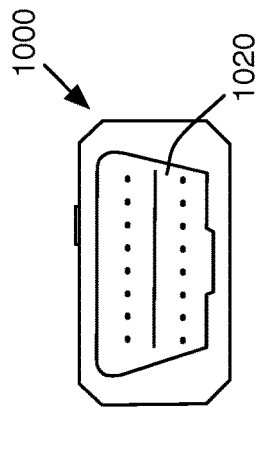
FIG. 10C is a front end view of the on-board diagnostics transceiver of FIGS. 10A and 10B.
Figure 10A:
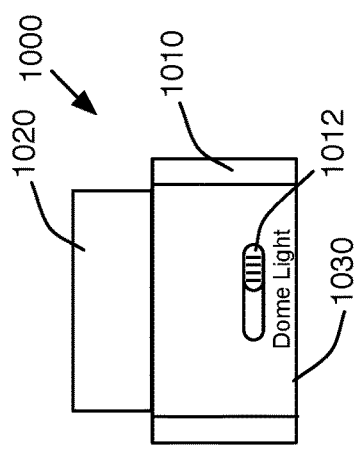
FIG. 10A is a top view illustration of a vehicle on-board diagnostics transceiver in accordance with one or more example embodiments.
Figure 10B:
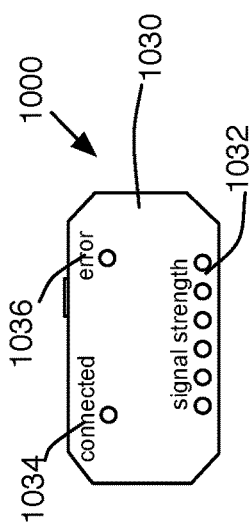
FIG. 10B is a rear end view of the on-board diagnostics transceiver of FIG. 10A.

Turning now to FIGS. 10A, 10B, and 10C, an example on-board vehicle diagnostics transceiver 1000 (also sometimes referred to herein as a vehicle bio-link or "BLINK") may be configured to communicate with ARC systems described herein. In some embodiments, transceiver 1000 may include a connector 1020 having pins or other features configured to interface with an OBD II port on a vehicle, or another data output port. A front end 1030, e.g. opposite connector 1020, may include a plurality of different indicators, e.g., for signal strength 1032, connection status 1034, and/or error status 1036. For example, signal strength 1032 may indicate the strength of a wireless connection with the ARC system (e.g., the connection between vehicle 200 and vehicle interface 950 of system 100).

In some embodiments, certain functions or features of the vehicle may be configured to be activated or controlled when the transceiver 1000 is in communication with the ARC system 100. For example, in some embodiments a vehicle dome light or other interior lighting may be activated by the system 100 and/or transceiver 1000. One or more switches 1012 or other devices or features may be incorporated to enable and/or disable such control.

In some embodiments, a vehicle diagnostics transceiver 1000 may be used to transmit vehicle diagnostic and/or identification information to the ARC system 100. For example, information such as vehicle VIN number, license plate number, mileage, maximum speed, maximum RPM, vehicle error codes, gas level, gas mileage or consumption, vehicle GPS information, or other desired information. In some embodiments, such collected information may be integrated into a report, e.g., by report processing module 958, or accessed by servers 860 or users 920, and/or stored in a database in the system 100, server 860, or remote database 850 for later access. For example, a rental car company or car dealership may use such information, along with records of vehicle dents, scratches or other damage detected by the system, to analyze the condition or usage of a vehicle.

IV. Example Methods

Figure 11A:
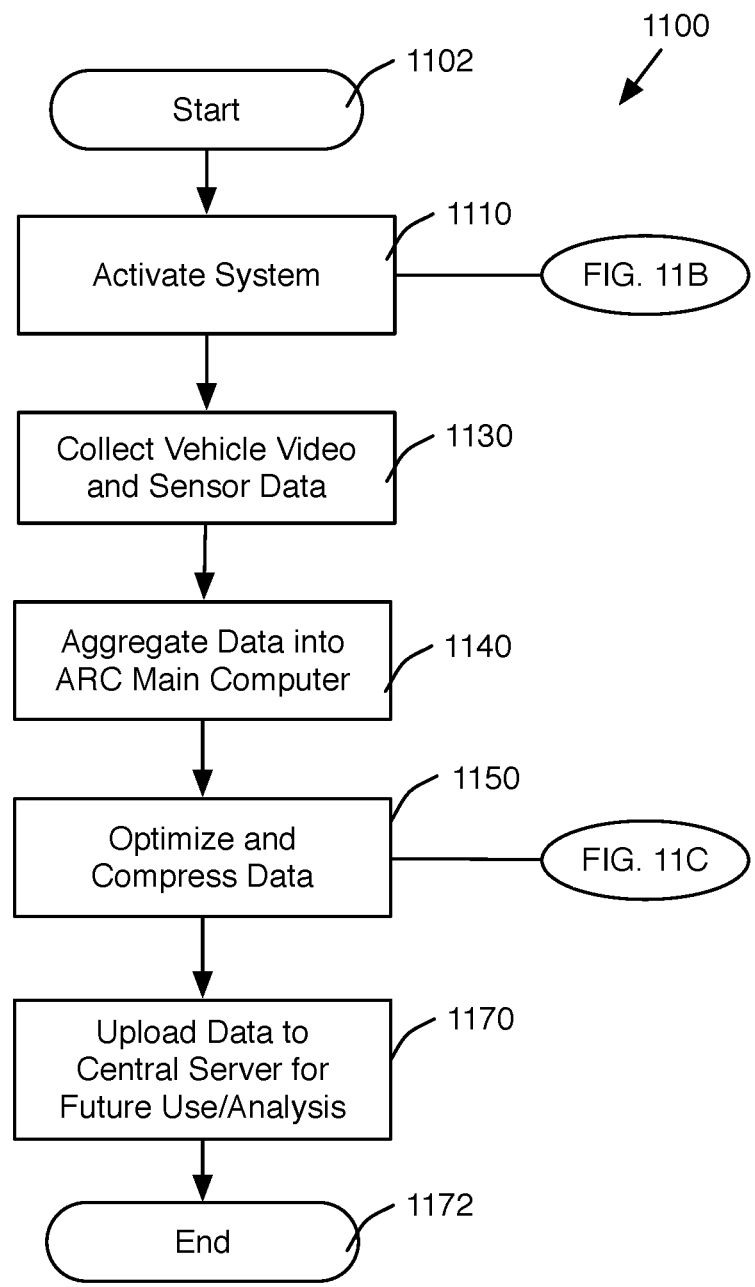
FIG. 11A is a flow chart of an example method of using an automated radial imaging system to in accordance with one or more example embodiments.
Figure 11B:
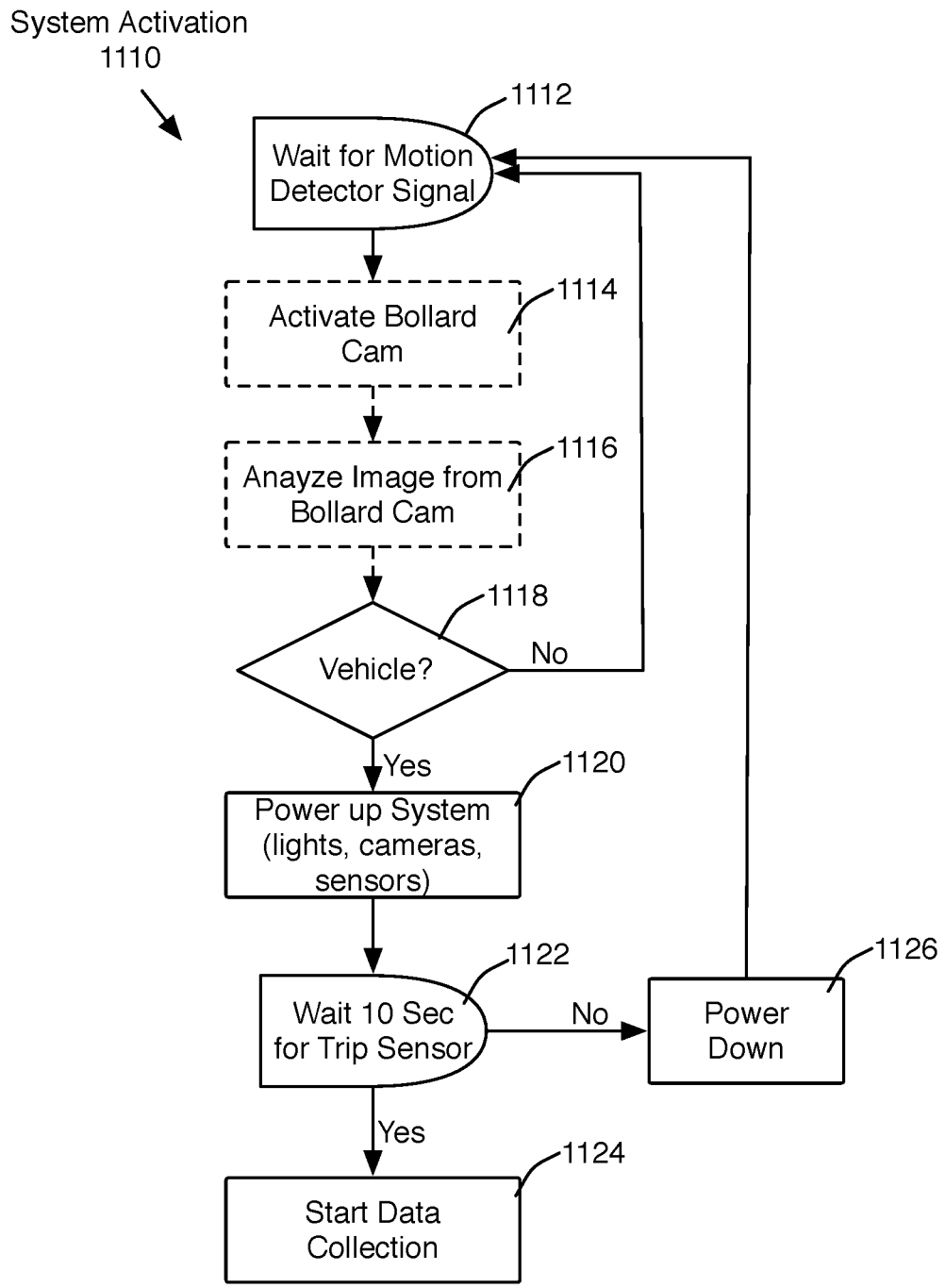
FIG. 11B is a flow chart of an example method of activating an automated radial imaging system in accordance with one or more example embodiments.
Figure 11C:
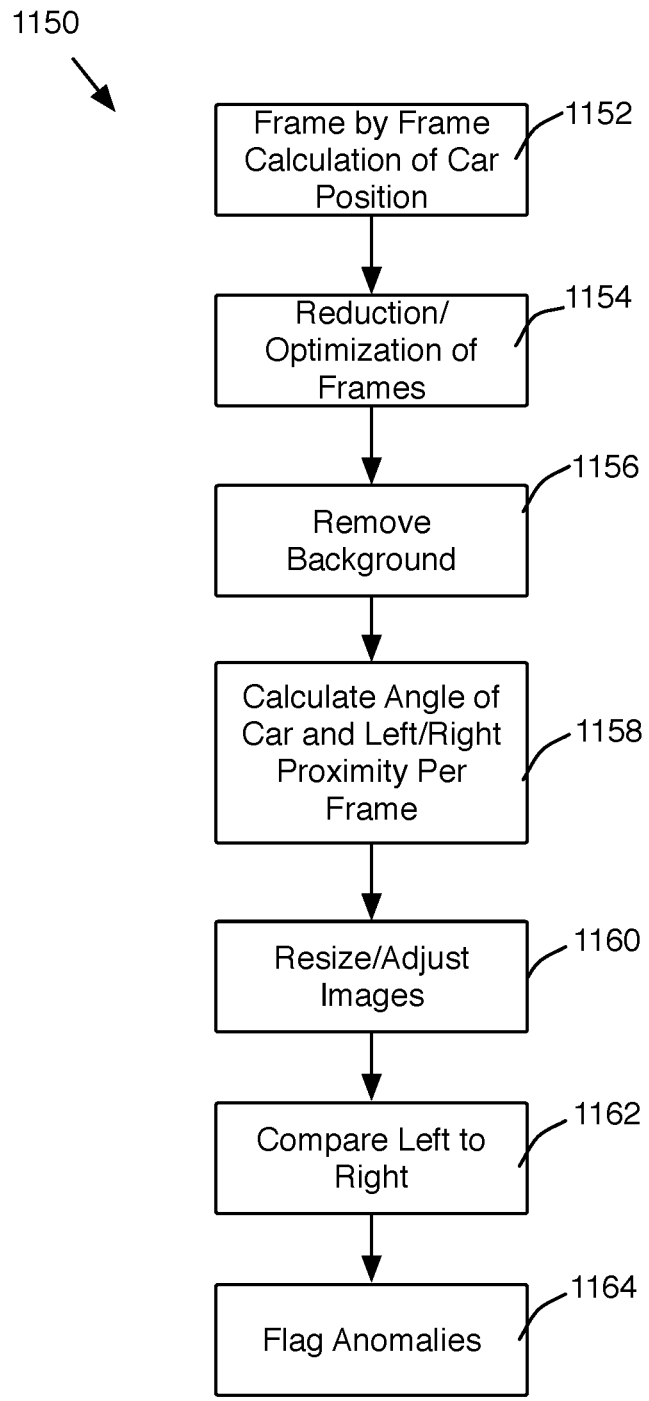
FIG. 11C is a flow chart of an example method of optimizing, compressing and analyzing vehicle image data in an automated radial imaging system in accordance with one or more example embodiments.

FIGS. 11A to 11C are flow charts describing various steps in an exemplary method 1100 of operating an automated radial imaging and analysis system in accordance with one or more example embodiments. Referring to FIG. 11A, an example method of operation 1100 may start 1102 with activation 1110. In some embodiments, activating 1110 the system may involve activating cameras, sensors and associated electronics. Activating the system (e.g., system 100 of FIG. 1) may also include activating lights, e.g., illuminating light panels 470 and/or other lights to illuminate a vehicle for optimal imaging and detection of any dents, dings, scratches, blemishes, or other deformities (collectively referred to herein as "anomalies").

In some embodiments, a user or technician may activate the system manually or on-demand, e.g., using a button, switch, or other manual or automated control signal. In some embodiments, one or more components or subsystems of an automated radial imaging and analysis system may be activated automatically in response to signals from one or more sensors, such as a motion detector (e.g., sensor 190 in FIG. 1). For example, a motion detector may detect the presence of a vehicle in front of or approaching the scanner system, and the system may activate (e.g., power on one or more cameras, sensors, electronic components, and/or lights) in response to such detection. Additional details and optional examples of activating 1110 the system are described below with respect to FIG. 11B.

Once the system is activated 1110, including preparing cameras, sensors (e.g., trip sensors in one or more bollards and/or proximity sensors in the frame of the apparatus and/or cross member), video images and sensor data (e.g., collectively "data") may be collected by the system, e.g., video captured by each camera in frame 110 and/or bollards 150, 152, 154, 156, and collected or aggregated by a unit controller or video collector 460 in each pod or group.

Collected data may be aggregated 1140 into the main computer 450 of the system 100, where it may be optimized, analyzed and/or compressed 1150, e.g., as shown and described in more detail below with respect to FIG. 11C.

Optimized and/or compressed data may be uploaded 1170 or otherwise transferred from system 100, e.g., over the Internet 840 or other network, to a central computer system (e.g., central server 860 of FIG. 8) for storage, future use, and/or analysis. The method 1100 may end in step 1172.

FIG. 11B shows additional details of a system activation step 1110 of FIG. 11A, in accordance with an example embodiment. In this example, the system controller or main computer 450 may wait 1112 for a signal from one or more motion detectors (e.g., detector 190 of FIG. 1), for example in response to the detector 190 sensing a vehicle or other object. In some embodiments, the motion detector 190 is a large-object detector capable of distinguishing between a vehicle and a person (or at least of ignoring the presence of a person or other small object). In such embodiments, the method may jump to step 1118 to determine the presence of a vehicle and power up the system 1120.

In some embodiments, one or more cameras and/or sensors may be used to determine if a nearby object is a vehicle to be scanned or a person or other small object to ignore. For example, a motion detection signal 1112 may activate 1114 one or more bollard cameras (e.g., in front of or behind the system frame with respect to the detected object, and/or cameras in the frame 110) to record one or more images or video of the object. In some embodiments, such images may be analyzed 1116 to detect the presence, position and/or orientation of a vehicle, and if a vehicle is present 1118, to power up the system 1120. In some embodiments, powering up the system 1120 may include activating cameras, sensors, lights, and/or associated electronic components of a system 100 to prepare for scanning of a vehicle.

In some embodiments, if the analysis in 1116 does not determine the presence of a vehicle 1118, the system returns to a sleep or standby mode, e.g., 1112 waiting for a signal from the motion detector(s) or other manual or automatic activation signal.

In some embodiments, after the system is powered up 1120, it may wait 1122 for a desired period of time, e.g., ten seconds, for one or more trip sensors, e.g., sensors 162 or 166, or other bollard sensors to detect a vehicle entering the system. If a trip sensor signal is not received in 1122, the system may power down after the defined period of time 1126. If a trip sensor is activated in 1122, data collection may begin 1124. In some embodiments, data collection will proceed until one or more sensors on an opposite side of the apparatus 100 (e.g., in the rear bollards) detect that the vehicle has passed (e.g., cleared the rear bollards). In other embodiments, data collection 1124 will continue for a defined period of time.

FIG. 11C shows additional optional details of the optimizing data in step 1150 of FIG. 11A. In this example, the ARC main computer 450 (or in some embodiments, a remote or distributed computer system) may calculate the vehicle's position 1152, e.g., by distance and angle measurements of camera and/or sensor data. Such calculation of car position 1152 may be performed on a frame by frame basis, and one or more frames or groups of frames may be removed, consolidated and/or selected to optimize the number of frames, the image quality, and/or the size of the video/image files to be analyzed.

In some embodiments, background of images may be removed 1156. In step 1158, the angle of the car and/or left/right position of the car may be analyzed for each frame. For example cameras 342, 344 in cross member 130 and the angle or position of vehicle relative to base plate 170 and/or other reference points may be used to determine the angle of the car, and one or more proximity sensors (e.g., sensor 452 of FIG. 4) in each leg may be used to determine position of the vehicle.

In step 1160, the vehicle proximity, angle, and/or position data may be used to resize and/or adjust images, e.g., to normalize or standardize images of the left and right sides of the vehicle for easy comparison.

In step 1162, video and/or still images of the left and right sides of the vehicle are compared to detect the presence of any dings, dents, scratches, blemishes or other anomalies in the vehicle. In some embodiments, the system may include software instructions or routines for performing such comparison in 1162 automatically. In other embodiments, the system may provide simultaneous video of the symmetrical sides of the vehicle to a user for visual analysis.

In step 1164, any detected anomalies may be flagged, e.g., the video files tagged, time stamped, and/or other means for indicating the presence of one or more defects or anomalies associated with the vehicle. In some embodiments, such image analysis results may be included in a report or file, any may include additional vehicle information such as vehicle identification information (e.g., from an image of the license plate or sensor data) and/or vehicle diagnostic information from an OBD II transceiver 1000 as described above.

Figure 12:
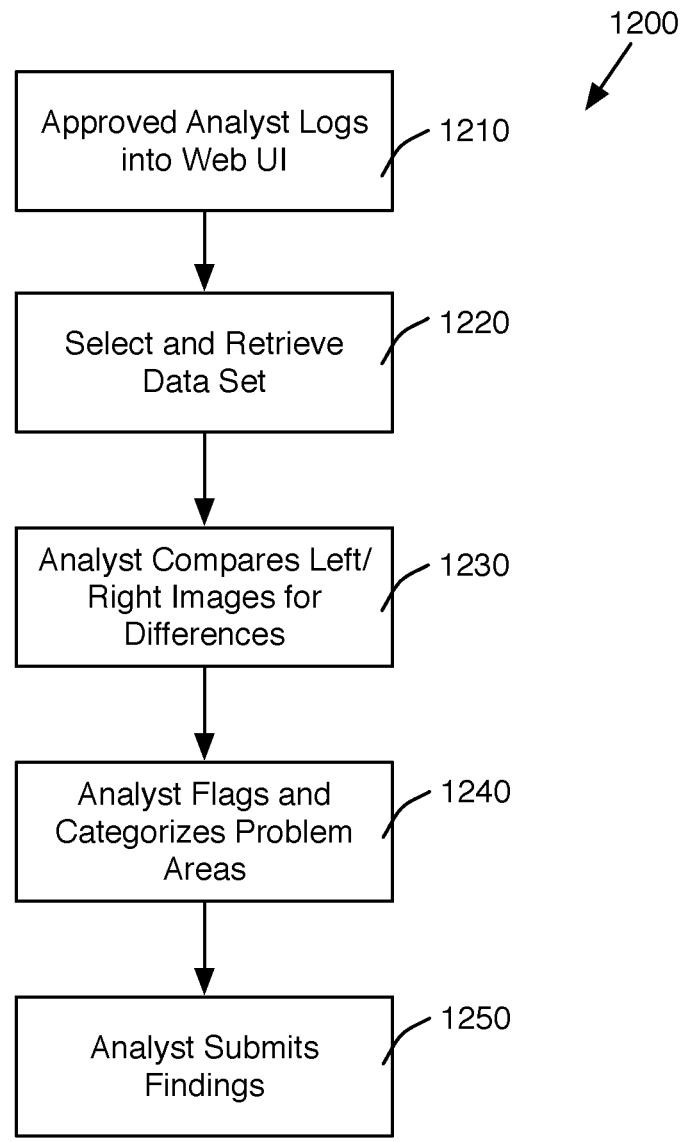
FIG. 12 is a flow chart of an example method of analyzing video images of a vehicle using a crowdsourcing application accordance with one or more example embodiments.

Turning now to FIG. 12, an example method 1200 of analyzing vehicle video information recorded by an automated radial imaging and analysis system is shown. In this example, the method 1200 is performed using an application, e.g., a crowdsourcing application 969 if FIG. 9, to allow authorized users to analyze video data to identify, confirm, and/or classify damage or other anomalies in a vehicle. For example, an approved analyst my log in 1210 to the Web Server user interface ("UP") of central server 860 (which may be or include one or more distributed servers and/or cloud services). The user may then select and retrieve 1220 (or download, for example) a vehicle data set to be analyzed. In some embodiments, the data set may include dual video streams or images of left and right sides of a vehicle recorded and processed by a scanner system 100.

In some embodiments, the analyst may then view the video to compare 1230 left and right images (or video streams) of the vehicle to detect or verify differences and/or potential anomalies. In some embodiments, the analyst may then flag and categorize 1230 anomalies (or problem areas), or in some cases confirm previously detected or flagged area. The analyst may then submit findings and/or a report associated with the analyzed video.

Figure 13:
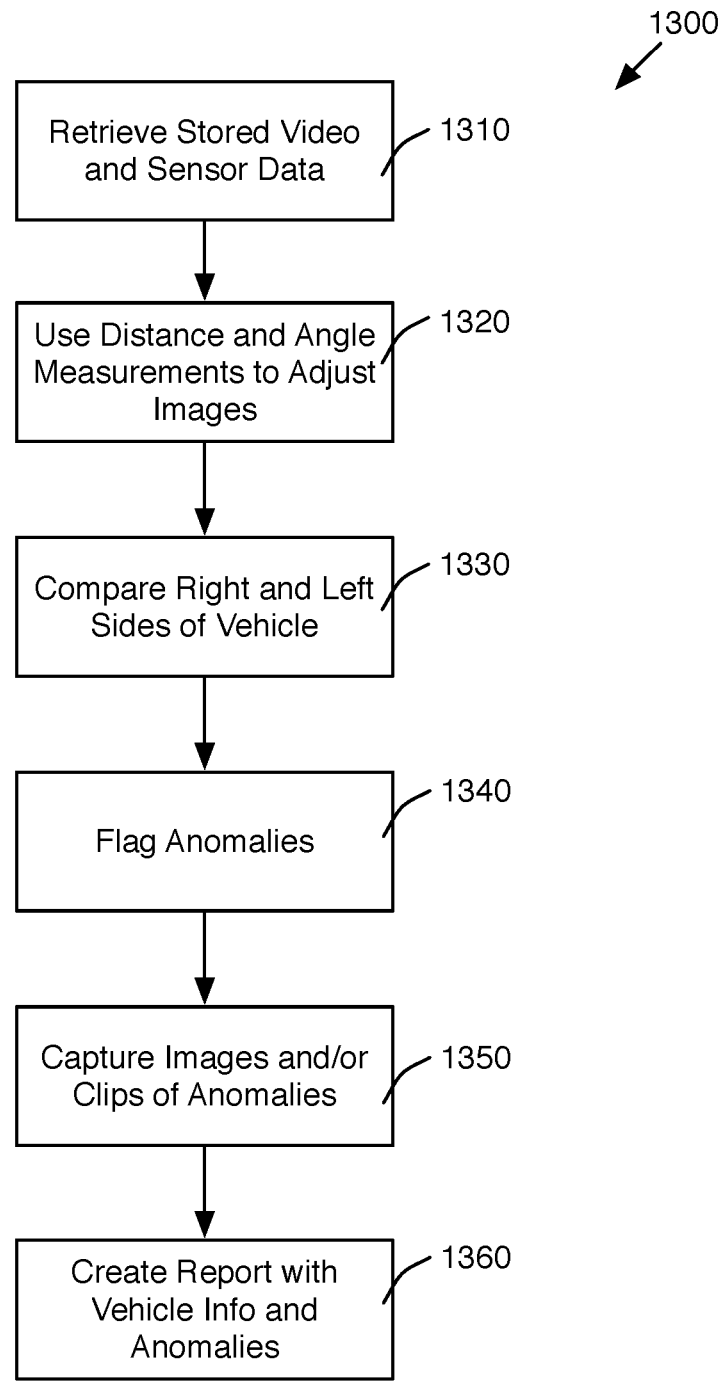
FIG. 13 is a flow chart of another example method of analyzing video images of a vehicle in accordance with one or more example embodiments.

FIG. 13 illustrates a method 1300 of automated analysis of collected and processed video, in accordance with one or more example embodiments. In this example, data analysis module 968 of central server 860 of FIG. 9 may include instructions or software routines for analyzing vehicle video images captured by a system 100. In step 1310, stored video and/or sensor data (e.g., data collected and processed as described above with respect to FIG. 11A) may be downloaded, retrieved, or otherwise accessed by the module 968. The system may use distance and angle measurements, e.g., from sensors in system 100, to adjust images if such adjustments were not previously performed, e.g., locally in ARC system computer 450 or in central server 860. In step 1330, video images of the right and left sides of the vehicle may be overlaid and/or otherwise compared to detect damage or other anomalies. Any detected anomalies may be flagged 1340, and selected images and/or video clips may be captured or extracted to highlight or otherwise show the anomalies. In step 1360, a report may be generated or created, and may include vehicle ID, detected anomalies (including location, type and/or severity of damage) and other information about the vehicle (e.g., vehicle diagnostic information from OBD II interface or transceiver as described herein).

Figure 14:
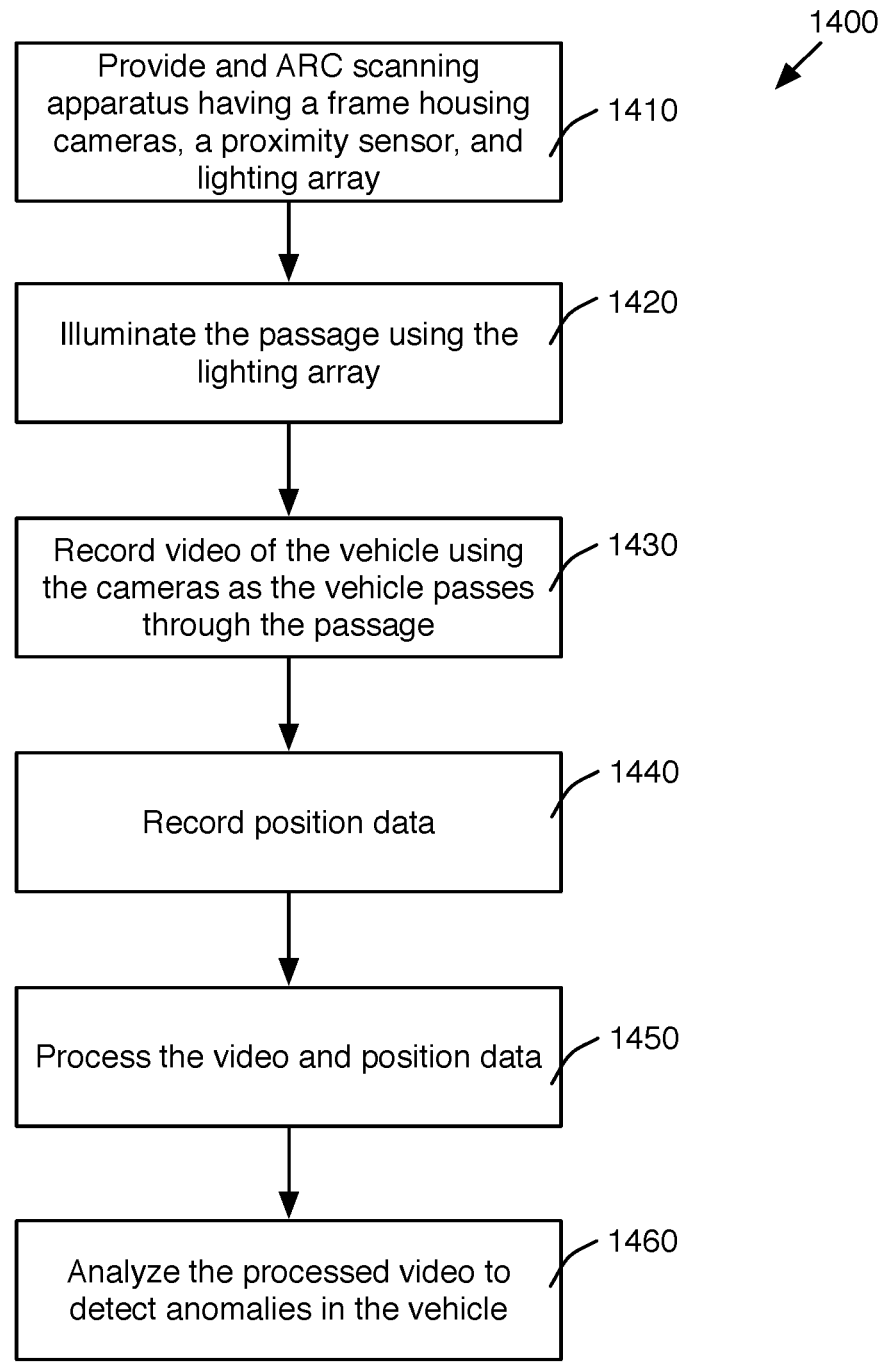
FIG. 14 is a flow chart of an example method of detecting damage to a vehicle using systems described herein.

Turning now to FIG. 14, another method 1400 of detecting damage to a vehicle is illustrated in accordance with one or more example embodiments. In step 1410, the method may include providing an apparatus having a frame surrounding a passage through which a vehicle may pass, wherein the apparatus houses a plurality of cameras, a proximity sensor, and a lighting array configured to illuminate the passage. In some embodiments, the lighting array may comprise a panel having plurality of elongated and substantially parallel LED lights separated by dark bands to illuminate the vehicle with a striped light pattern to facilitate detection of the anomalies.

A next step may include illuminating 1420 the passageway using the lighting array, e.g., to provide light of a desired quality or intensity for imaging the vehicle. In some embodiments, the lighting array may comprise a panel having plurality of elongated and substantially parallel LED lights separated by dark bands to illuminate the vehicle with a striped light pattern to facilitate detection of the anomalies. In some embodiments, the apparatus may also include a motion detector, and the method may further include the step of receiving an activation signal from the motion detector before activating the lighting array to illuminate the passage.

A next step may include recording video 1430 of the vehicle using the cameras as the vehicle passes through the passage. In some embodiments, providing the apparatus may further include providing a pair of front bollards on a front side of the frame and pair or rear bollards on a side of the frame opposite the front bollards, wherein recording video further comprises capturing images from front bollard cameras housed within the front bollards and from rear bollard cameras housed within the rear bollards.

Additional steps may include recording position data 1440 indicating a position of the vehicle relative to the frame using the proximity sensor, processing 1450 the video and position data to adjust the size of images in the video to correct for variations in the position of the vehicle, and analyzing 1460 the processed video to detect anomalies in the vehicle.

In some embodiments, recording video 1430 may include recording simultaneous video images of the right side of the vehicle and of the left side of the vehicle. Analyzing the processed video 1460 may then include comparing the video images of the right side of the vehicle with the video images of the left side of the vehicle to detect the anomalies. In some embodiments, analyzing the processed video 1460 may further include synchronizing and simultaneously presenting the video images of the right sight of the vehicle and video images of the left side of the vehicle over a network to an analyst to detect and flag the anomalies.

In other embodiments, other methods of processing and/or analyzing vehicle data captured by the system may be employed without departing from the scope of the subject matter herein.

V. Conclusion

The foregoing description illustrates various embodiments along with examples of how aspects of the systems may be implemented. The above examples and embodiments should not be deemed to be the only embodiments, and are presented to illustrate the flexibility and advantages of the systems as defined by the following claims. In the figures, similar symbols typically identify similar components, unless context dictates otherwise. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the sequence diagrams and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the diagrams, scenarios, and flow charts discussed herein, and these diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). Functional aspects described as modules need not be arranged or stored as a unit, and may include instructions, routines or program code distributed, stored and executed in any manner. The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, flash drives, compact-disc read only memory (CD-ROM), for example. The computer readable media may also be any other volatile or non-volatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices. Similarly, while some processors, computer systems or servers are depicted for purposes of illustration as a single device or module, one skilled in the art will appreciate that the corresponding hardware and software components may be distributed among several computer systems, processors, servers, cloud services or other systems.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A vehicle imaging system, comprising:
    a frame having a central passage, wherein the central passage is configured and dimensioned to allow a vehicle to pass through the central passage;
    a plurality of cameras disposed within the frame, each of said cameras directed to record images of a vehicle passing through the passage;
    one or more frame sensors disposed within the frame, including a proximity sensor for determining a distance of the vehicle with respect to the frame;
    a light source integrated within said frame, said light source for illuminating the passage; and
    a controller disposed within the frame, said controller for controlling the cameras, the one or more frame sensors, and the light source;
    wherein the frame further comprises a first leg, second leg, and a cross member spanning between the first leg and the second leg and defining the central passage; further comprising a pair of front bollards positioned on a front side of the frame and a pair of rear bollards positioned on a rear side of the frame, wherein at least one of the front bollards and at least one of the rear bollards each includes a bollard camera directed toward the central passage of the frame.

2. The system of claim 1, wherein the light source is configured to illuminate the vehicle passing through the central passage and the cameras are positioned to record video images of the vehicle.

3. The system of claim 2, wherein the light source further comprises one or more lighting array panels comprising a plurality of elongated and parallel LED channels for emitting an array of parallel bands of light towards the central passage of the frame.

4. The system of claim 3, further comprising a base plate having a plurality of parallel bands of reflective material corresponding to the plurality of elongated and parallel LED channels in the frame.

5. The system of claim 1, wherein the distance between said bollards in each of the front pair and the rear pair is less than or equal to a width of the central passage between the first leg and second leg of the frame.

6. The system of claim 5, wherein each of the front pair and rear pair of bollards includes at least one bollard sensor.

7. The system of claim 6, wherein the at least one bollard sensor is a trip sensor configured for detecting an object passing between the two bollards in each of the front pair and the rear pair of bollards.

8. The system of claim 7, wherein each leg includes a pod comprising two or more of the plurality of cameras, at least a portion of the one or more frame sensors, and a video collector for collecting data from the two or more cameras and the at least a portion of the one or more frame sensors.

9. The system of claim 1, wherein the one or more frame sensors further includes a motion detector in communication with the controller, wherein the motion detector is configured to detect the presence of an object near the frame, and the controller includes instructions for activating the plurality of cameras and the light source in response to a signal from the motion detector.

10. The system of claim 9, further comprising a guide secured between first and second legs of the frame, said guide configured and dimensioned to fit between the wheel and under the chassis of the vehicle when the vehicle passes through the central passage.

11. The system of claim 1, wherein said controller comprises a vehicle interface configured to wirelessly communicate with a wireless transceiver in the vehicle to receive and store vehicle identification and diagnostic information.

12. The system of claim 11, wherein the vehicle identification and diagnostic information comprises any of the vehicle identification number, gas mileage, volume of fuel, engine codes, or GPS information obtained from an OBD II port on the vehicle.

13. A method, comprising:
    providing an apparatus having a frame surrounding a passage through which a vehicle may pass, said apparatus housing a plurality of cameras, a proximity sensor, and a lighting array configured to illuminate the passage;
    illuminating the passage using the lighting array;
    recording video of the vehicle using the cameras as the vehicle passes through the passage;
    recording position data indicating a position of the vehicle relative to the frame using the proximity sensor;

processing the video and position data to adjust the size of images in the video to correct for variations in the position of the vehicle; and analyzing the processed video to detect anomalies in the vehicle;

wherein recording video comprises recording simultaneous video images of the right side of the vehicle and of the left side of the vehicle; and wherein analyzing the processed video comprises comparing the video images of the right side of the vehicle with the video images of the left side of the vehicle to detect the anomalies.

14. The method of claim 13, wherein analyzing the processed video further comprises synchronizing and simultaneously presenting the video images of the right sight of the vehicle and video images of the left side of the vehicle over a network to an analyst to detect and flag the anomalies.

15. The method of claim 13, wherein the lighting array comprises a panel having plurality of elongated and parallel LED lights separated by dark bands to illuminate the vehicle with a striped light pattern to facilitate detection of the anomalies.

16. The method of claim 15, wherein the apparatus further comprises a motion detector, said method further comprising the step of receiving an activation signal from the motion detector before said illuminating the passage.

17. The method of claim 13, wherein:

said providing the apparatus further comprises providing a pair of front bollards on a front side of the frame and pair or rear bollards on a side of the frame opposite the front bollards, and said recording video further comprises capturing images from front bollard cameras housed within the front bollards and from rear bollard cameras housed within the rear bollards.

* * * * *